(12) United States Patent
Geva et al.

(10) Patent No.: US 11,000,519 B2
(45) Date of Patent: May 11, 2021

(54) PRIDOPIDINE FOR TREATING DRUG INDUCED DYSKINESIAS

(71) Applicant: PRILENIA NEUROTHERAPEUTICS LTD., Herzliya (IL)

(72) Inventors: Michal Geva, Even-Yehuda (IL); Aric Orbach, Rehovot (IL); Michael Hayden, Herzliya (IL)

(73) Assignee: PRILENIA NEUROTHERAPEUTICS LTD., Herzliya (IL)

(*) Notice: Subject to any disclaimer, the term of this patent is extended or adjusted under 35 U.S.C. 154(b) by 0 days.

(21) Appl. No.: 16/436,947

(22) Filed: Jun. 11, 2019

(65) Prior Publication Data

US 2019/0350914 A1   Nov. 21, 2019

Related U.S. Application Data

(63) Continuation of application No. 16/377,577, filed on Apr. 8, 2019, which is a continuation-in-part of
(Continued)

(51) Int. Cl.
  *A61K 31/445* (2006.01)
  *A61K 31/451* (2006.01)
  (Continued)

(52) U.S. Cl.
  CPC .......... *A61K 31/451* (2013.01); *A61K 9/0053* (2013.01); *A61K 45/06* (2013.01);
  (Continued)

(58) Field of Classification Search
  CPC .................................................. A61K 31/451
  (Continued)

(56) References Cited

U.S. PATENT DOCUMENTS

| 6,903,120 B2 | 6/2005 | Sonesson et al. |
| 7,417,043 B2 | 8/2008 | Sonesson et al. |

(Continued)

FOREIGN PATENT DOCUMENTS

| WO | WO 2001/046145 | 6/2001 |
| WO | WO 2006/040155 | 4/2006 |

(Continued)

OTHER PUBLICATIONS

Ahlskog, J, E., & Muenter, M. D. (2001). Frequency of levodopa-related dyskinesiasand motor fluctuations as estimated from the cumulative literature. *Movement disorders: official journal of the Movement Disorder Society*, 16(3), 448-458.

(Continued)

*Primary Examiner* — Shengjun Wang
(74) *Attorney, Agent, or Firm* — Mark S. Cohen; Pearl Cohen Zedek Latzer Baratz LLP

(57) ABSTRACT

The invention provides a method of treating a subject afflicted with a drug-induced movement disorder including levodopa-induced dyskinesia comprising periodically administering to the subject in need thereof an amount of pridopidine effective to treat the subject. The invention further provides a method of treating a subject at risk of developing a drug-induced movement disorder, including levodopa-induced dyskinesia. The invention also provides pharmaceutical compositions suitable for carrying out these methods and packages containing such pharmaceutical compositions.

20 Claims, 10 Drawing Sheets

Related U.S. Application Data application No. PCT/US2018/048920, filed on Aug. 30, 2018.

(60) Provisional application No. 62/649,184, filed on Mar. 28, 2018, provisional application No. 62/556,314, filed on Sep. 8, 2017.

(51) Int. Cl.
*A61P 25/14* (2006.01)
*A61K 45/06* (2006.01)
*A61P 25/16* (2006.01)
*A61K 9/00* (2006.01)
*A61K 31/198* (2006.01)

(52) U.S. Cl.
CPC .............. *A61P 25/14* (2018.01); *A61P 25/16* (2018.01); *A61K 31/198* (2013.01)

(58) Field of Classification Search
USPC ........................................................ 514/317
See application file for complete search history.

(56) References Cited

U.S. PATENT DOCUMENTS

| | | | |
|---|---|---|---|
| 7,923,459 B2 | 4/2011 | Gauthier et al. | |
| 9,006,445 B2 | 4/2015 | Sonesson et al. | |
| 9,012,476 B2 | 4/2015 | Zimmermann et al. | |
| 9,139,525 B2 | 9/2015 | Wikstrom | |
| 9,796,673 B2 | 10/2017 | Wu et al. | |
| 9,814,706 B2 | 11/2017 | Zimmermann et al. | |
| 10,047,049 B2 | 8/2018 | Barel et al. | |
| 10,130,621 B2 | 11/2018 | Schmidt et al. | |
| 10,322,119 B2 | 6/2019 | Bassan et al. | |
| 2008/0234321 A1* | 9/2008 | Sonesson ............. | C07D 211/24 514/317 |
| 2013/0150406 A1* | 6/2013 | Zimmermann ...... | C07D 211/24 514/317 |
| 2013/0197031 A1 | 8/2013 | Sonesson | |
| 2013/0267552 A1 | 10/2013 | Waters et al. | |
| 2014/0315951 A1* | 10/2014 | Sonesson ............. | C07D 211/30 514/317 |
| 2015/0202302 A1 | 7/2015 | Licht et al. | |
| 2016/0095847 A1 | 4/2016 | Sonesson et al. | |
| 2016/0166559 A1 | 6/2016 | Sonesson et al. | |
| 2016/0243098 A1 | 8/2016 | Geva et al. | |
| 2017/0020854 A1 | 1/2017 | Chen et al. | |
| 2017/0266170 A1 | 9/2017 | Waters et al. | |
| 2018/0055832 A1 | 3/2018 | Hayden et al. | |
| 2018/0235950 A1 | 8/2018 | Sonesson et al. | |
| 2019/0015401 A1 | 1/2019 | Sonesson | |
| 2019/0030016 A1 | 1/2019 | Schmidt et al. | |
| 2019/0046516 A1 | 2/2019 | Russ et al. | |
| 2019/0192496 A1 | 6/2019 | Hayden et al. | |
| 2019/0209542 A1 | 7/2019 | Licht et al. | |

FOREIGN PATENT DOCUMENTS

| | | |
|---|---|---|
| WO | WO 2008/127188 | 10/2008 |
| WO | WO 2008/155357 | 12/2008 |
| WO | WO 2012/002863 | 3/2012 |
| WO | WO 2013/034622 | 3/2013 |
| WO | WO 2013/086425 | 6/2013 |
| WO | WO 2013/152105 | 10/2013 |
| WO | WO 2014/205229 | 12/2014 |
| WO | WO 2015/112601 | 7/2015 |
| WO | WO 2015/003919 | 1/2016 |
| WO | WO 2015/138130 | 9/2016 |
| WO | WO 2017/015609 | 1/2017 |
| WO | WO 2017/015615 | 1/2017 |
| WO | WO 2017/147366 | 8/2017 |
| WO | WO 2018/039475 | 3/2018 |
| WO | WO 2018/039477 | 3/2018 |
| WO | WO 2018/053275 | 3/2018 |
| WO | WO 2018/053287 | 3/2018 |
| WO | WO 2019/053280 | 3/2018 |
| WO | WO 2018/136600 | 7/2018 |
| WO | WO 2019/036358 | 2/2019 |
| WO | WO 2019/046568 | 3/2019 |

OTHER PUBLICATIONS

Bargiotas, P., & Konitsiotis, S. (2013). Levodopa-induced dyskinesias in Parkinson's disease: emerging treatments. *Neuropsychiatric disease and treatment*, 9, 1605.

Brod, S. A., Lindsey, J. W., & Wolinsky, J. S, (2000), Combination therapy with glatiramer acetate (copolymer-1) and a type I interferon (Ifn-a) does not improve experimental autoimmune encephalomyelitis. Annals of neurology, 47(1), 127-131.

Brust, P., Deuther-Conrad, W., Lehmkuhl, K., Jia, H., & Wünsch, B. (2014). Molecular imaging of σ1 receptors in vivo: current status and perspectives. *Current medicinal chemistry*, 21(1), 35-69.

CSID:25948790, www.chemspider.com/Chemical-Structure.25948790. html (accessed 23:27, Jul. 15, 2016).

CSID:7971505, www.chemspider.com/Chemical-Structure.79715 E5.html (accessed 23:33, Jul. 15, 2018).

Cubo, E. Grades, J. M, Benabau, R, Olanow, C. W., Raman, R., Leurgans, S., & Goetz, C. G. (2001). Early morning off-medication dyskinasias, dystonia, and choreic subtypes. *Archives of neurology*, 58(9), 1379-1382.

Daneault, J. F., Carignan, B., Sadikot, A. F., Panisset, M., & Duval, C. (2013). Drug-induced dyskinesia in Parkinson's disease. Should success in clinical management be a function of improvement of motor repertoire rather than amplitude of dyskinesia?. *BMC medicine*, 11(1), 76.

Dizdar, N., Kullman, A., Norlander, B., Olsson, J. E., & Kågedal, B. (1999). Human pharmacokinetics of L-3, 4-dihydroxyphenylalanine studied with microdialysis. *Clinical chemistry*, 45(10), 1813-1820.

Food and Drug Administration. The Voice of the Patient, Parkinson's Disease. Public Meeting, Sep. 22, 2015. Report date Apr 2016 [cited Dec. 21, 2018].

Gerber, P. E., & Lynd, L. D. (1998). Selective serotonin-reuptake inhibitor-induced movement disorders. *Annals of Pharmacotherapy*, 32(6), 692-698.

Geva, M., Kusko, R., Soares, H., Fowler, K. D., Birnberg, T., Barash, S., . . . & Cha, Y. (2016). Pridopidine activates neuroprotective pathways impaired in Huntington Disease. *Human molecular genetics*, 25(18), 3975-3987.

Goetz, C. G., Fahn, S., Martinez-Martin, P., Poewe, W., Sarnpaio, C., Stebbins, G. T., . . . & Holloway, R. (2007). Movement Disorder Society-sponsored revision of the Unified Parkinson's Disease Rating Scale (MDS-UPDRS): process, format, and clinimetric testing plan. *Movement Disorders*, 22(1), 41-47.

Goetz, C. G., Nutt, J. G., & Stebbins, G. T. (2008). The unified dyskinesia rating scale: presentation and clinirmetric profile. *Movement disorders: official journal of the Movement Disorder Society*, 23(16), 2398-2403.

Goetz, C. G., Stebbins, G. T., Chung, K. A., Hauser, R. A., Miyasaki, J. M., Nicholas, A. P., . . . & Nutt, J. G. (2013). Which dyskinesia scale best detects treatment response?. *Movement Disorders*, 28(3), 341-346.

Goetz, C. G., Tilley, B. C., Shaftman, S. R., Stebbins, G. T., Fahrr, S., Martinez-Martin, P., . . . & Dubois, B. (2008). Movement Disorder Society-sponsored revision of the Unified Parkinson's Disease Rating Scale (MDS-UPDRS): scale presentation and clinimetric testing results. *Movement disorders: official journal of the Movement Disorder Society*, 23(15), 2129-2170.

Guy, W. E. (1976). ECDEU assessment manual for psychopharmacology-revised (DHEW Publ No. ADM 76-338). Rockville, MD, US Department of Health, Education, and Welfare. Public Health Service, Alcohol, Drug Abuse, and Mental Health Administration, NIMH Psychopharmacology Research Branch, Division of Extramural Research Programs, 1076, 534-7.

Hauser, R. A., Rascol, O., Korczyn, A. D., Jon Stoessl, A., Watts, R. L., Poewe, W., . . . & Lang, A. E. (2007). Ten-year follow-up of Parkinson's disease patients randomized to initial therapy with

(56) References Cited

OTHER PUBLICATIONS ropinirole or levodopa. *Movement Disorders*, 22(161 2409-2417.
Huot, P., Johnston, T. H., Koprich, J. B., Fox, S. H., & Brotchie, J. M. (2012), L-DOPA pharmacokinetics in the MPTP-lesioned macaque model of Parkinson's disease. Neuropharmacology. 63(5), 829-836.
Huot, P., Johnston, T. H., Koprich, J. B., Fox, S. H., & Brotchie, J. M. (2013). L-DOPA pharmacokinetics in the MPTP-lesioned macque model of Parkinson's disease. Neuropharmacology, 63(5), 829-836.
Huot, P., Johnston, T. H., Koprich, J. B., Fox, S. H., & Brotchie, J. M. (2013). The pharmacology of L-DOPA-induced dyskinesia in Parkinson's disease. *Pharmacological reviews*, 65(1), 171-222.
International Search Report dated Dec. 3, 2018 for PCT/US2018/048920.
Jenner, P. (2008). Molecular mechanisms of L-DOPA-induced dyskinesia. *Nature Reviews Neuroscience*, 9(9), 665.
Johnston, T. H., Huot, P., Fox, S. H., Koprich, J. B., Szeliga, K. T., James, J. W., . . . & Brotchie, J. M. (2013). TC-8831, a nicotinic acetylcholine receptor agonist, reduces L-DOPA-induced dyskinesia in the MPTP macaque. *Neuropharmacology*, 73, 337-347.
Johnston, T. H., Geva, M., Steiner, L., Orbach, A., Papapetropoulos, S., Savola, J. M., . . . & Brotchie, J. M. (2019). Pridopidine, a clinic-ready compound, reduces 3, 4-dihydroxyphenylalanine-induced dyskinesia in Parkinsonian macaques. *Movement Disorders*, 34(5), 708-716.
Kumar, N., Van Gerpen, J. A., Bower, J. H., & Ahlskog, J. E. (2005). Levodopa-dyskinesia incidence by age of Parkinson's disease onset. *Movement disorders*, 20(3), 342-344.
Lee, C. S. (2001). Levodopa-induced dyskinesia: Mechanisms and management. *British Columbia Medical Journal*, 43(4), 206-209.
Manson, A., Stirpe, P., & Schrag, A. (2012). Levodopa-induced-dyskinesias clinical features, incidence, risk factors, management and impact on quality of life. *Journal of Parkinson's disease*, 2(3), 189-198.
Marder, K., Zhao, H., Myers, R. H., Cudkowicz, M., Kayson, E., Kieburtz, K., . . . & Shoulson, I. (2000). Rate of functional decline in Huntington's disease. *Neurology*, 54(2), 452-452.
Movement Disorder Society Task Force on Rating Scales for Parkinson's Disease. (2003). The unified Parkinson's disease rating scale (UPDRS): status and recommendations. *Movement Disorders*, 18(7), 738-750.
National Research Council. (2010). *Guide for the care and use of laboratory animals*. National Academies Press.
Parkinson Study Group. (2004). Levodopa and the progression of Parkinson's disease. *New England Journal of Medicine*, 351(24), 2498-2508.
PDR 2017 Amantadine hydrochloride—Drug Summary, PDR (Prescribers' Digital Reference), http://www.pdr.net/drug-summary/Amantadine-Hydrochloride-Capsules-amantadine-hydrochloride-1475 accessed Sep. 7, 2017.
PDR 2017 Amantadine hydrochloride—Drug Summary, PDR (Prescribers' Digital Reference), http://www.pdr.net/drug-summary/Amantadine-Hydrochloride-Tablets-amantadine-hydrochloride-2441 accessed Sep. 7, 2017.
Poewe, W., & Mahlknecht, P. (2009). The clinical progression of Parkinson's. disease. *Parkinsonism & related disorders*, 15, S28-S32.
Ponten, H., Kullingsjö, J., Lagerkvist, S., Martin, P., Pettersson, F., Sonesson, C., . . . & Waters, N. (2010). In vivo pharmacology of the dopaminergic stabilizer pridopidine. *European journal of pharmacology*, 644(1-3), 88-95.
Ponten, H., Kullingsjö, J., Sonesson, C., Waters, S., Waters, N., & Tedroff, J. (2013). The dopaminergic stabilizer pridopidine decreases expression of L-DOPA-induced locomotor sensitisation in the rat unilateral 6-OHDA model. *European journal of pharmacology*, 698(1-3), 278-285.
Rascol, O., Brooks, D. J., Korczyn, A. D., De Deyn, P. P., Clarke, C. E., & Lang, A. E. (2000). A five-year study of the incidence of dyskinesia in patients with early Parkinson's disease who were treated with ropinirole or levodopa. *New England Journal of Medicine*, 342(20), 1484-1491.
Sahlholm, K., Århem, P., Fuxe, K., & Marcellino, D. (2013). The dopamine Stabilizers ACR16 and (-)-OSU6162 display nanomolar affinities at the $\sigma$-1 receptor. *Molecular psychiatry*, 18(1), 12.
Sahlholm, K., Sijbesma, J. W., Maas, B., Kwizera, C., Marcellino, D., Ramakrishnan, N. K., . . . & van Waarde, A. (2015). Pridopidine selectively occupies sigma-1 rather than dopamine D2 receptors at behaviorally active doses. *Psychopharmacology*, 232(18), 3443-3453.
Shoulson, I., & Fahn, S. (1979). Huntington disease: clinical care and evaluation. *Neurology*, 29(1), 1-1.
Slifstein, M., Kegeles, L. S., Xu, X., Thompson, J. L., Urban, N., Castrillon, J., . . . & Abi-Dargham, A. (2010). Striatal and extrastriatal dopamine release measured with PET and [18F] fallypride. *Synapse*, 64(5), 350-362.
Tedroff, J., Sonesson, C., Waters, N., Waters, S., & Carlsson, A. (Jan. 2004). A pilot study of the novel dopamine stabiliser ACR16 in advanced Parkinson's disease, In *Movement Disorders* (vol. 19, pp. S201-S202), Div John Wiley & Sons Inc, 111 River St, Hoboken, NJ 07030 USA: Wiley-Liss.
Thanvi, B., Lo, N., & Robinson, T. (2007). Levodopa-induced dyskinesia in Parkinson's disease: clinical features, pathogenesis, prevention and treatment. *Postgraduate medical journal*, 83(980), 384-388.
De Yebenes, J. G, et al. (2011)—Pridopidine for the treatment of motor function in patients with Huntington's disease (MermaiHD): a phase 3, randomized, double-blind, placebo-controlled trial. The Lancet Neurolog, vol. 10, not 12, p. 1049-1057.
Huntington Study Group Hart Investigators (2013)—A randomized, double-blind, placebo-controlled trial of pridopidine in Huntington's disease. Movement Disorders, vol. 28, not 10, pp. 1407-1415. First published Feb. 28, 2013.
Rabinovich-Guilatt et al. (2016)—The effect of mild and moderate renal impairment on the pharmacokinetics of pridopidine, a new drug for Huntington's disease—British journal of clinical pharmacology, 81(2), 246-255.

\* cited by examiner

| | Placebo | 45 mg bid | 112.5 mg bid |
|---|---|---|---|
| N | 81 | 75 | 81 |
| Baseline | 7.9 | 8.1 | 8 |
| Δ to placebo | | 0.87 | 0.24 |
| p value | | 0.0032 | 0.4061 |

PRIDOPIDINE FOR TREATING DRUG INDUCED DYSKINESIAS

CROSS REFERENCE TO RELATED APPLICATIONS

This application is a Continuation of U.S. patent application Ser. No. 16/377,577 filed on Apr. 8, 2019, which is a continuation-in-part of International Application No. PCT/US2018/048920, filed Aug. 30, 2018, which claims the benefit of U.S. Provisional Application No. 62/556,314, filed Sep. 8, 2017, and of U.S. Provisional Application No. 62/649,184, filed Mar. 28, 2018, the entire contents of which are hereby incorporated by reference herein.

BACKGROUND

Drug Induced Dyskinesias

Dyskinesias are abnormal, involuntary movements which may appear as jerking, twisting or writhing of parts of the body. There are several different types of dyskinesias, which can be categorized as chorea, dystonia, myoclonus, tremor and paroxysmal tardive (late-onset type). Drug-induced movement disorders (DIMDs) may be elicited by different pharmaceutical agents, which modulate dopamine neurotransmission as well as other neurotransmission in the central nervous system such as serotonin, adrenaline and acetylcholine neurotransmission. The major groups of drugs responsible for DIMDs include antidepressants, antipsychotics, antiepileptics, antimicrobials, antiarrhythmics, mood stabilisers and gastrointestinal drugs, among others. These movement disorders include, without limitation, parkinsonism, tardive dyskinesia, chorea, dystonia, tremor, akathisia, athetosis, myoclonus or tics.

Parkinson's Disease and Levodopa-Induced Dyskinesias

Parkinson's disease (PD) is a degenerative disorder characterized by the loss of substantia nigra pars compacta dopaminergic neurons and the subsequent loss of dopaminergic input to the striatum. As the degenerative process evolves, dopamine replacement therapy becomes necessary to help alleviate motor dysfunction.

Dyskinesias are common in Parkinson's disease (PD) and can be separated into a) dyskinesias resulting from the disease process itself, and b) dyskinesias that are the side-effect of levodopa medication given to treat symptoms of PD (Levodopa-Induced Dyskinesia, LID) (Cubo 2001).

Levodopa (L-DOPA), the most effective agent to alleviate motor dysfunction in Parkinson's disease patients, is associated with the development of dyskinesias with chronic use. L-DOPA Induced Dyskinesia (LID) is a major complication of dopamine-replacement therapy in PD ("PD-LID"; Kumar 2005, Manson 2012, Poewe 2009). Other dopamine agonist therapies may induce dyskinesia in PD patients.

The levodopa-induced dyskinesias occur in the majority of the PD patients and initially are mild, progressing to a complex and severe disorder that interferes with motor function, speech, coordination and social activity. LID can adversely affect the quality of life for Parkinson's disease patients.

Peak-dose dyskinesias are the most prevalent type of dyskinesia. They occur during peaks of levodopa-derived dopamine in the brain, when the patient is otherwise experiencing a beneficial response (the 'on' state). Peak dose dyskinesias worsen with increases in dopaminergic therapy and lessen with reductions in dopaminergic therapy. Some patients exhibit diphasic dyskinesia, which occurs when levodopa-derived dopamine concentrations are increasing or decreasing and the patient is shifting between 'on' and 'off' states.

The therapeutic and preventative strategies for LID include using a lower dosage of levodopa, employing other dopamine agonists as initial therapy in Parkinson's disease, amantadine, atypical neuroleptics, and neurosurgery.

The potential of pridopidine to reduce motor complications of L-DOPA in PD was reported using the 6-OHDA-lesioned rat model (Ponten 2013). The data from that rat 6-OHDA study suggests that low doses of pridopidine, up to about 67.5 mg bid may be efficacious against PD-LID.

Tedroff, 2004, reported an open label, uncontrolled, self-assessed, pilot study of once a day low-dose pridopidine (20-100 mg once a day; average dose 57 mg/day) in seven advanced stage Parkinson's disease (PD) patients. Tedroff provides no guidance for treating LID in PD patients. Since that study was disclosed with no mention of what the "regular antiparkinsonias medication" is, no controlled study has been performed to objectively assess the effect of pridopidine for treating LID in PD patients.

Pridopidine

Pridopidine (formerly ACR16, Huntexil®, TV-7820) is a drug in development for the treatment of patients with Huntington's disease. The chemical name of pridopidine base is 4-(3-(methylsulfonyl)phenyl)-1-propylpiperidine, and its Chemical Registry Number is CAS 346688-38-8 (CSID:7971505, 2016). The Chemical Registry number of pridopidine hydrochloride is 882737-42-0 (CSID:25948790 2016).

Pridopidine demonstrates a complex binding profile with high affinity binding to the sigma-1 receptor ($\sigma_1 R$, or S1R) (Internal studies; Sahlholm 2013,) and low affinity binding to several other CNS targets, including receptors for dopamine, serotonin, 5-HT1A, 5-HT2A and 5-HT7; adrenergic alpha-1, adrenergic alpha-2A and alpha-2C receptors, dopamine D3 and dopamine D2 (D2R) receptors; and muscarinic M2 and histamine H3 receptors (Internal studies, Ponten 2013).

Pridopidine has been shown to modulate motor activity by either suppressing hyperactivity or enhancing hypoactivity. The neuroprotective properties of pridopidine are suggested to be attributed to its high affinity to the S1R, while the motor activity of pridopidine may be mediated primarily by its moderate-affinity targets, including antagonistic activity at the dopamine D2 receptor (Ponten 2010, Sahlholm 2015).

The S1R is an endoplasmic reticulum (ER) chaperone protein which is implicated in cellular differentiation, neuroplasticity, neuroprotection and cognitive function in the brain. Recently, transcriptomic analysis of rat striatum showed that pridopidine treatment activates expression of the brain-derived neurotrophic factor (BDNF), dopamine receptor 1 (D1R), glucocorticoid receptor (GR), and the serine-threonine kinase protein kinase B (Akt)/phosphoinositide 3-kinase (PI3K) pathways, known to promote neuronal plasticity and survival and to be impaired in HD. Pridopidine was shown to enhance secretion of the neuroprotective BDNF in a neuroblastoma cell line, in a S1R-dependent manner (Geva 2016).

Effective treatments for LID and other drug induced movement disorders (DIMD), including drug-induced dyskinesias, remain a significant unmet need.

SUMMARY OF THE INVENTION

The present invention is based at least in part on evidence from in vivo studies that high doses of pridopidine are efficacious in treating symptoms of drug induced dyskinesias, including PD-LID.

This evidence is especially surprising in view of the lack of efficacy of high doses of pridopidine in improving motor function in HD patients.

The present invention provides a method of treating LID in a subject with PD comprising administering to the subject an amount of pridopidine effective to treat the LID in the subject. The present invention also provides a method of treating LID in a subject with parkinsonism other than PD comprising administering to the subject an amount of pridopidine effective to treat the LID in the subject.

The present invention also provides a method for treating dyskinesia induced by a drug other than levodopa, for example an anti-depressant or an anti-psychotic comprising administering to the subject an amount of pridopidine effective to treat the dyskinesia in the subject.

The present invention additionally provides a method of treating a subject afflicted with a drug-induced movement disorder (DIMD). The invention further provides a method for treatment of a DIMD in a subject in need thereof comprising periodically administering to the subject an amount of pridopidine effective to treat the DIMD. The invention also provides pridopidine for use in treating drug-induced movement disorder (DIMD) in a subject in need thereof. In some embodiments, the DIMD comprises dyskinesia. In some embodiments the dyskinesia is levodopa-induced dyskinesia (LID). In some embodiments, the DIMD is induced by a drug selected from an antidepressant, an antipsychotic, an antiepileptic, an antimicrobial, an antiarrhythmic, a mood stabilizer, a gastrointestinal drug or any combination thereof. Certain selective serotonin reuptake inhibitors (SSRI) are known to induce DIMD (Gerber 1998, incorporated herein in its entirety by reference). In some embodiments, the DIMD is selected from parkinsonism, tardive dyskinesia, chorea, dystonia, tremor, akathisia, athetosis, myoclonus or tics.

The invention further provides a method of treating a subject afflicted with a side effect of levodopa treatment comprising administering to the subject an amount of pridopidine effective to treat the subject. The invention provides pridopidine for use in treating a side effect of levodopa treatment in a subject in need thereof.

This invention further provides a method of treating a human subject afflicted with a levodopa induced dyskinesia comprising periodically administering to the subject an amount of levodopa and an amount of pridopidine or a salt thereof, wherein the amounts when taken together are effective to treat the human subject. Further provided is pridopidine in combination with levodopa for use in treating levodopa induced dyskinesia in a subject in need thereof. In some embodiments of the method and use, the subject is afflicted with parkinsonism. In some embodiments of the method and use, the subject is a patient afflicted with Parkinson's disease.

The invention further provides a method of treating a subject at risk of developing a drug-induced movement disorder, including levodopa-induced dyskinesia, comprising administering to the subject an amount of pridopidine effective to delay the onset of LID or reduce the risk of developing LID.

In embodiments of the method and use for treating LID in PD patients, or of the method and use of treating a subject at risk of developing LID, the amount of pridopidine administered is greater than 100 mg/day up to 400 mg/day. In certain embodiments, the amount of pridopidine administered is 112.5 mg/day, 125 mg/day, 135 mg/day, 150 mg/day, 175 mg/day, 180 mg/day, 200 mg/day, 225 mg/day, 250 mg/day, 300 mg/day, 350 mg/day, or 400 mg/day.

In embodiments of the method and use for treating LID, or of the method and use of treating a subject at risk of developing LID, the AUC0-inf 24 achieved is 12,000 h*ng/ml to 60,000 h*ng/ml, or 20,000 h*ng/ml-60,000 h*ng/ml, or 25,000 h*ng/ml-60,000 h*ng/ml or at least 29,000 h*ng/ml up to about 60,000 h*ng/ml.

This invention also provides a package comprising (a) a first pharmaceutical composition comprising an amount of levodopa and a pharmaceutically acceptable carrier; (b) a second pharmaceutical composition comprising an amount of pridopidine and a pharmaceutically acceptable carrier. In a further embodiment, the package also comprises (c) instructions for use of the first and second pharmaceutical compositions together to treat a human subject afflicted with LID or DIMD. In some embodiments the pridopidine is provided as pridopidine base. In some embodiments the pridopidine is provided as a pridopidine salt, e.g. pridopidine HCl.

This invention additionally provides use of an amount of levodopa and an amount of pridopidine in the preparation of a combination for treating a human subject afflicted with a levodopa induced dyskinesia wherein the levodopa or pharmaceutically acceptable salt thereof and the pridopidine are administered simultaneously or contemporaneously. This invention additionally provides use of an amount of amantadine, or levodopa and amantadine, and an amount of pridopidine in the preparation of a combination for treating a human subject afflicted with a levodopa induced dyskinesia wherein the levodopa, or levodopa and amantadine, and the pridopidine are administered simultaneously or contemporaneously.

This invention also provides a pharmaceutical composition comprising an amount of levodopa for use in treating a subject afflicted with levodopa induced dyskinesia as an add-on therapy or in combination with pridopidine by periodically administering the pharmaceutical composition and the pridopidine to the subject.

This invention also provides a pharmaceutical composition comprising an amount of pridopidine for use treating a subject afflicted with levodopa induced dyskinesia as an add-on therapy or in combination with levodopa and/or amantadine by periodically administering the pharmaceutical composition to the subject.

In yet another embodiment of the methods, uses and compositions, the dyskinesia in a subject afflicted with PD is quantified by the Movement Disorder Society Unified Parkinson's Disease Rating Scale (MDS-UPDRS) score, wherein an increase in the MDS-UPDRS score represents progression of Parkinson's disease symptoms, and the increment of the increase in total UPDRS score over a period of time represents the rate of progression of Parkinson's disease symptoms (Goetz 2007, Goetz 2008a, the entire contents of which are hereby incorporated by reference). In some embodiments, the dyskinesia in a subject afflicted with PD is quantified using the PD Home Diary scale. In other embodiment of the methods, uses and compositions, the dyskinesia in a subject not afflicted with PD is quantified by, for example, the Unified Dyskinesia Rating Scale (UdysRS) or AIMS rating scale (Goetz 2008b, Ecdeu 1976, the entire contents of which are hereby incorporated by reference).

BRIEF DESCRIPTION OF THE FIGURES

FIGS. 1A and 1B: Graphs showing the effect of 45 mg bid pridopidine on Total Motor Score (TMS), full analysis set from MermaiHD (FIG. 1A) and HART (FIG. 1B) studies, respectively. In both graphs, the upper line shows results with placebo treatment, the lower line shows results with 45 mg bid treatment.

FIG. 2: Bar graph showing the effect of 45 mg bid or 112.5 mg bid pridopidine on change from baseline in Total Motor Score (TMS) in early stage HD Patients (baseline TFC≥11) at week 52 in the PRIDE-HD study. A decrease in TMS from baseline indicates improvement (table below the graph).

FIG. 3: bar graph showing the effect of 45 mg bid or 112.5 mg bid pridopidine on change from baseline in Total Functional Capacity (TFC), full analysis, at week 52 by treatment group in the PRIDE-HD study. An increase in TFC from baseline indicates improvement (table below the graph).

FIGS. 5A,5B-10 show the effect of pridopidine in combination with a high L-DOPA dose in a MPTP-lesioned non-human primate (NHP) model with established motor complications in two studies. The figures provide data showing that pridopidine reduced L-DOPA induced dyskinesia, including choreiform and dystonic dyskinesia evoked by high-dose L-DOPA without affecting the beneficial anti-parkinsonian effects of L-DOPA.

FIG. 5A: Graph showing dyskinesia (time course 0-6 hr) (study 2): Pridopidine reduces established dyskinesia evoked by high L-DOPA. Y axis is severity of dyskinesia, X axis shows time course, 0-6 hr. FIG. 5B: Bar graph showing dyskinesia (0-2 hr accumulated) (study 2): Pridopidine reduces established dyskinesia evoked by high dose L-DOPA. Y axis is severity of dyskinesia, X axis shows pridopidine doses.

FIG. 10: Bar graph showing the effects of pridopidine on duration and quality of on-time (study 2).

DETAILED DESCRIPTION OF THE INVENTION

Figure 1A:
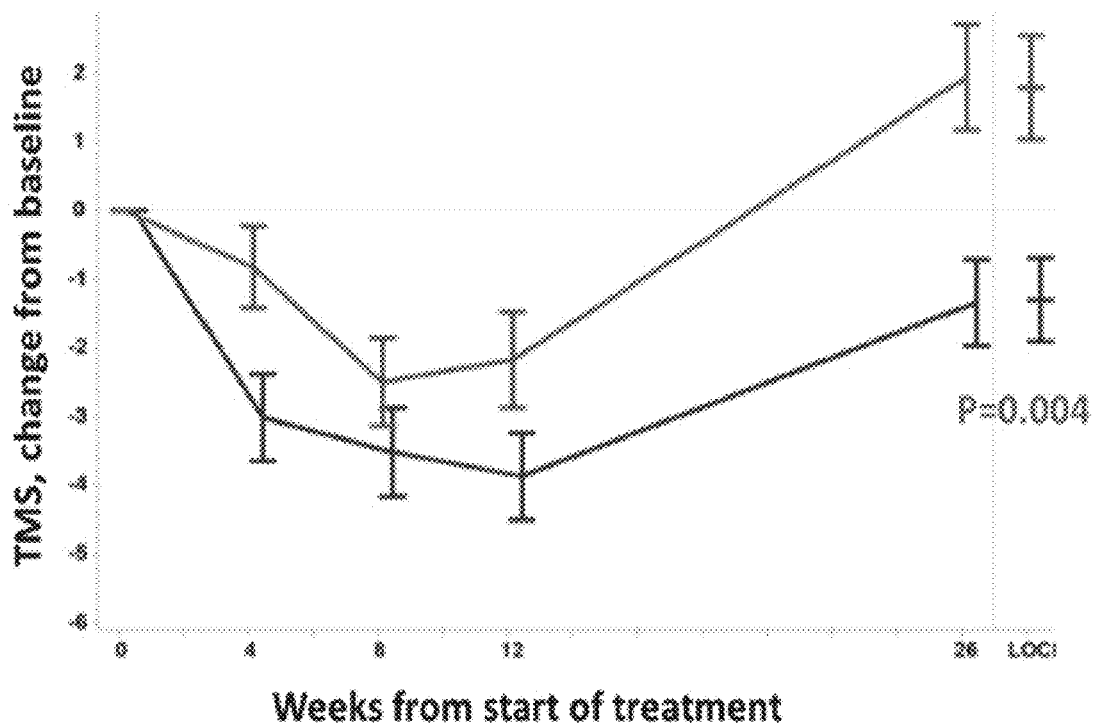
FIGS. 1A, 1B, 2 and 3 show the effect of pridopidine in historic studies of Huntington's disease.

The present invention provides a method of treating a subject afflicted with a drug-induced movement disorder (DIMD) comprising periodically administering to the subject an amount of pridopidine effective to treat the subject. The invention further provides a method for the treatment of a DIMD comprising periodically administering to a subject in need thereof an amount of pridopidine effective to treat the DIMD. In some embodiments, the DIMD comprises dyskinesia.

In an embodiment, the dyskinesia is Levodopa-Induced Dyskinesia (LID).

The invention also provides a method of treating a subject afflicted with a side effect of levodopa treatment comprising administering to the subject an amount of pridopidine effective to treat the subject.

In another embodiment, treating comprises reducing a side effect of levodopa. In one embodiment, the side effect is dyskinesia.

In some embodiments, the subject is a patient afflicted with parkinsonism. In one embodiment, the subject is a Parkinson's disease patient. In another embodiment, the subject is an advanced stage Parkinson's disease patient. In a further embodiment, the subject is a patient afflicted with parkinsonism other than Parkinson's disease.

In one embodiment, the subject is concurrently being treated with levodopa.

In an embodiment, the amount of pridopidine and the levodopa are administered simultaneously. In another embodiment, the amount of pridopidine and the levodopa are co-formulated. In another embodiment, the amount of pridopidine and the levodopa are administered sequentially and in separate pharmaceutical formulations.

In one embodiment, the amount of pridopidine is effective to alleviate or reduce a symptom associated with the levodopa treatment. In some embodiments, the symptom is dyskinesia, abnormal movements, myoclonic jerks, irregular movements of extremities, gait, facial grimacing, ataxia, inability to sustain motor act, hand movement or balance. In another embodiment, the symptom is choreiform peak dose dyskinesia, or dystonic peak dose dyskinesia. In another embodiment, the symptom is bad quality on-time evoked by levodopa.

In an embodiment, the administration of pridopidine improves the symptom of the levodopa induced dyskinesia by at least 8%, by at least 10%, by at least 15%, by at least 20%, by at least 30% or by at least 50% as measured by the Unified Dyskinesia Rating Scale (UDysRS) (Unified Dyskinesia Rating Scale (UDysRS) 2008, the entire content of which is hereby incorporated by reference).

In one embodiment, the anti-parkinsonian effect of levodopa is not affected by the amount of pridopidine.

In an embodiment, the dyskinesia in the subject is assessed by one or more of the following rating scales: UDysRS, UPDRS or AIMS (Unified Dyskinesia Rating Scale (UDysRS) 2008; Unified Parkinson's Disease Rating Scale (UPDRS): status and recommendations. 2003, Ecdeu 1976, the entire content of each of which is hereby incorporated by reference). In another embodiment, the patient had a UDysRS score or UPDRS score of 10 or greater at baseline.

In some embodiments, the DIMD is induced by a drug selected from an antidepressant, an antipsychotic, an antiepileptic, an antimicrobial, an antiarrhythmic, a mood stabilizer, a gastrointestinal drug or any combination thereof. The DIMD may be selected from parkinsonism, tardive dyskinesia, chorea, dystonia, tremor, akathisia, athetosis, myoclonus or tics. In some embodiments the DIMD is parkinsonism. In some embodiments the DIMD is tardive dyskinesia. In some embodiments the DIMD is drug-induced dystonia. In some embodiments the DIMD is tremor. In some embodiments the DIMD is akathisia. In some embodiments the DIMD is athetosis. In some embodiments the DIMD is myoclonus. In some embodiments the DIMD is tics.

In one embodiment, the pridopidine is administered via oral administration. In another embodiment, the pridopidine is administered once or twice daily. In another embodiment, pridopidine is administered twice daily. In another embodiment, pridopidine is administered thrice daily. In another embodiment, the pridopidine is a pridopidine base. In another embodiment, the pridopidine is a pridopidine salt. In another embodiment, the pridopidine salt is provided as pridopidine hydrochloride (pridopidine HCl).

In embodiments of the method or use for treating LID in PD patients, the amount of pridopidine administered to a subject in need thereof is 112.5 mg/day, 125 mg/day, 135 mg/day, 150 mg/day, 180 mg/day, 200 mg/day, 225 mg/day, 250 mg/day, 300 mg/day, 350 mg/day, 375 mg/day or 400 mg/day. In another embodiment, the amount of pridopidine administered is from above 100 mg per day to 400 mg per day. In another embodiment, the amount of pridopidine administered is from above 200 mg per day to 350 mg per day. In another embodiment, the amount of pridopidine administered is from above 100 mg per day to 350 mg per day. In another embodiment, the amount of pridopidine administered is more than 100 mg per day to 400 mg per day. In another embodiment, the amount of pridopidine administered is 200 mg per day. In another embodiment, the amount of pridopidine administered is 300 mg per day. In another embodiment, the amount of pridopidine administered is 350 mg per day. In some embodiments, the amount of pridopidine is administered once daily. In some embodiments, the amount of pridopidine is administered twice daily. In some embodiments, the amount of pridopidine administered is 75 mg tid (thrice daily), 90 mg tid, 100 mg tid, or 125 mg tid. In another embodiment, the amount of pridopidine administered is 100 mg bid (twice daily), 125 mg bid, 150 mg bid, 175 mg bid, or 200 mg bid. In preferred embodiments, the pridopidine is administered as pridopidine HCl, twice daily.

In embodiments of the method or use for treating LID in PD patients, the amount of pridopidine administered is from about 75 mg bid to about 200 mg bid. In one embodiment, the amount of pridopidine administered is from about 80 mg bid to about 200 mg bid. In one embodiment, the amount of pridopidine administered is from about 90 mg bid to about 200 mg bid. In one embodiment, the amount of pridopidine administered is from about 100 mg bid to about 200 mg bid. In one embodiment, the amount of pridopidine administered is from about 125 mg bid to about 200 mg bid. In one embodiment, the amount of pridopidine administered is from about 150 mg bid to about 200 mg bid. In one embodiment, the amount of pridopidine administered is from about 175 mg bid to about 200 mg bid.

In one embodiment, the amount of pridopidine administered is from about 75 mg bid to about 175 mg bid. In one embodiment, the amount of pridopidine administered is from about 75 mg bid to about 150 mg bid. In one embodiment, the amount of pridopidine administered is from about 75 mg bid to about 125 mg bid. In one embodiment, the amount of pridopidine administered is from about 75 mg bid to about 100 mg bid.

In one embodiment, the amount of pridopidine administered is from about 90 mg bid to about 175 mg bid. In one embodiment, the amount of pridopidine administered is from about 100 mg bid to about 175 mg bid. In one embodiment, the amount of pridopidine administered is from about 100 mg bid to about 150 mg bid. In one embodiment, the amount of pridopidine administered is from about 125 mg bid to about 150 mg bid. In one embodiment, the amount of pridopidine administered is from about 125 mg bid to about 175 mg bid. In one embodiment, the amount of pridopidine administered is from about 150 mg bid to about 200 mg bid.

In one embodiment, the pridopidine is administered about 100 mg bid. In one embodiment, the pridopidine is administered about 125 mg bid. In one embodiment, the pridopidine is administered about 150 mg bid. In one embodiment, the pridopidine is administered about 175 mg bid. In one embodiment, the pridopidine is administered about 200 mg bid.

In one embodiment, the pridopidine is administered orally. In one embodiment, the pridopidine is administered about 100 mg bid orally. In one embodiment, the pridopidine is administered about 125 mg bid orally. In one embodiment, the pridopidine is administered about 150 mg bid orally. In one embodiment, the pridopidine is administered about 175 mg bid orally. In one embodiment, the pridopidine is administered about 200 mg bid orally In embodiments of the method or use for treating LID in PD patients, pridopidine is administered at a daily dose of about 200 mg given in the form of pridopidine salt. A person of skill in the art would know that when pridopidine is administered at a daily dose of 200 mg given in the form of pridopidine salt, the 200 mg of the daily dose refers to 200 mg of pridopidine in its neutral/base form. A skilled artisan would know how much pridopidine salt is needed to contain 200 mg of pridopidine. In embodiments of the method or use for treating LID in PD patients, pridopidine is administered at a daily dose of about 225 mg given in the form of pridopidine salt. In embodiments of the method or use for treating LID in PD patients, pridopidine is administered at a daily dose of about 250 mg given in the form of pridopidine salt. In embodiments of the method or use for treating LID in PD patients, pridopidine is administered at a daily dose of about 275 mg given in the form of pridopidine salt. In embodiments of the method or use for treating LID in PD patients, pridopidine is administered at a daily dose of 300 mg given in the form of pridopidine salt. In embodiments of the method or use for treating LID in PD patients, pridopidine is administered at a daily dose of about 325 mg given in the form of pridopidine salt. In embodiments of the method or use for treating LID in PD patients, pridopidine is administered at a daily dose of about 350 mg given in the form of pridopidine salt. In embodiments of the method or use for treating LID in PD patients, pridopidine is administered at a daily dose of about 375 mg given in the form of pridopidine salt. In embodiments of the method or use for treating LID in PD patients, pridopidine is administered at a daily dose of about 400 mg given in the form of pridopidine salt. In preferred embodiments of the method or use for treating LID in PD patients, the specified dosage of pridopidine is administered in two equal doses.

In preferred embodiments of the method or use for treating LID in PD patients, the AUC0-24 achieved is about 25,000 h*ng/ml to about 60,000 h*ng/ml.

In certain embodiments of the method of treating LID in PD patients, pridopidine is administered to a subject in need thereof in an amount to achieve an $AUC_{0-24}$ plasma level of greater than 12,000 h*ng/ml to about 60,000 h*ng/ml, 20,000 h*ng/ml to 60,000 h*ng/ml, 25,000 h*ng/ml to 60,000 h*ng/ml, 29,000 h*ng/ml to 60,000 h*ng/ml, 15,000 h*ng/ml to 45,000 h*ng/ml, 15,000 h*ng/ml to 40,000 h*ng/ml, 20,000 h*ng/ml to 55,000 h*ng/ml, 20,000 h*ng/ml to 50,000 h*ng/ml, 20,000 h*ng/ml to 45,000 h*ng/ml, 20,000 h*ng/ml to 40,000 h*ng/ml, 20,000 h*ng/ml to 35,000 h*ng/ml, 20,000 h*ng/ml to 30,000 h*ng/ml, or about 13,000 h*ng/ml, 14,000 h*ng/ml, 15,000 h*ng/ml, 16,000 h*ng/ml, 17,000 h*ng/ml, 18,000 h*ng/ml, 19,000 h*ng/ml, 20,000 h*ng/ml, 21,000 h*ng/ml, 22,000 h*ng/ml, 23,000 h*ng/ml, 24,000 h*ng/ml, 25,000 h*ng/ml, 26,000 h*ng/ml, 27,000 h*ng/ml, 28,000 h*ng/ml, 29,000 h*ng/ml, 30,000 h*ng/ml, 31,000 h*ng/ml, 32,000 h*ng/ml, 33,000 h*ng/ml, 34,000 h*ng/ml, 35,000 h*ng/ml, 36,000 h*ng/ml, 37,000 h*ng/ml, 38,000 h*ng/ml, 39,000 h*ng/ml, 40,000 h*ng/ml, 41,000 h*ng/ml, 42,000 h*ng/ml, 43,000 h*ng/ml, 44,000 h*ng/ml, 45,000 h*ng/ml, 46,000 h*ng/ml, 47,000 h*ng/ml, 48,000 h*ng/ml, 49,000 h*ng/ml, 50,000 h*ng/ml, 51,000 h*ng/ml, 52,000 h*ng/ml, 53,000 h*ng/ml, 54,000 h*ng/ml, 55,000 h*ng/ml, 56,000 h*ng/ml, 57,000 h*ng/ml, 58,000 h*ng/ml, 59,000 h*ng/ml, or 60,000 h*ng/ml, In some embodiments, pridopidine is administered to a subject in need thereof in an amount to achieve an $AUC_{0-24}$ plasma level of 25,000 h*ng/ml to 60,000 h*ng/ml, 29,000 h*ng/ml to 59,000 h*ng/ml, or 29,000 h*ng/ml to 50,000 h*ng/ml, or about 25,000 h*ng/ml, 26,000 h*ng/ml, 27,000 h*ng/ml, 28,000 h*ng/ml, 29,000 h*ng/ml, 44,000 h*ng/ml, 45,000 h*ng/ml, 46,000 h*ng/ml, 50,000 h*ng/ml, 51,000 h*ng/ml, or 52,000 h*ng/ml.

In some embodiments wherein the patient is suffering from LID, the method further comprises administering to the subject a therapeutically effective amount of levodopa.

In embodiments of the method or use for treating DIMD other than LID in PD patients, the amount of pridopidine administered to the subject is 22.5 mg/day, 45 mg, 67.5 mg/day, 75 mg/day, 90 mg/day, 100 mg/day, 112.5 mg/day, 125 mg/day, 135 mg/day, 150 mg/day, 180 mg per day, 225 mg/day, 250 mg/day, 270 mg/day, 275 mg/day, 300 mg/day, 350 mg/day, 360 mg/day, 375 mg/day or 400 mg/day.

In embodiments of the method or use for treating DIMD other than LID in PD patients, pridopidine is administered at a daily dose of 45 mg given in the form of pridopidine salt. In embodiments of the method or use for treating DIMD other than LID in PD patients, pridopidine is administered at a daily dose of 90 mg given in the form of pridopidine salt. In embodiments of the method or use for treating DIMD other than LID in PD patients, pridopidine is administered at a daily dose of 135 mg given in the form of pridopidine salt. In embodiments of the method or use for treating DIMD other than LID in PD patients, pridopidine is administered at a daily dose of 180 mg given in the form of pridopidine salt. In embodiments of the method or use for treating DIMD other than LID in PD patients, pridopidine is administered at a daily dose of 200 mg given in the form of pridopidine salt. In embodiments of the method or use for treating DIMD other than LID in PD patients, pridopidine is administered at a daily dose of 225 mg given in the form of pridopidine salt. In embodiments of the method or use for treating DIMD other than LID in PD patients, pridopidine is administered at a daily dose of 250 mg given in the form of pridopidine salt. In embodiments of the method or use for treating DIMD other than LID in PD patients, pridopidine is administered at a daily dose of 300 mg given in the form of pridopidine salt. In embodiments of the method or use for treating DIMD other than LID in PD patients, pridopidine is administered at a daily dose of 350 mg given in the form of pridopidine salt. In embodiments of the method or use for treating DIMD other than LID in PD patients, pridopidine is administered at a daily dose of 400 mg given in the form of pridopidine salt. In preferred embodiments of the method or use for treating DIMD other than LID in PD patients, the daily dose of pridopidine is administered in two equal doses.

In some embodiments, for example where the subject is afflicted with LID, the method further comprises administering to the subject a therapeutically effective amount of a second compound which is levodopa and/or amantadine. In some embodiments, the subject is administered pridopidine and levodopa. In some embodiments, the subject is administered pridopidine and amantadine. In some embodiments, the subject is administered pridopidine, levodopa and amantadine. In an embodiment, the pridopidine and the second compound (e.g. levodopa, amantadine or levodopa and amantadine) are administered in one unit. In another embodiment, the pridopidine and the second compound are administered in more than one unit.

In one embodiment, the second compound is amantadine. In another embodiment, the amount of amantadine is 10 mg-400 mg. In another embodiment, the amount of amantadine is 10 mg, 20 mg, 30 mg, 40 mg, 50 mg, 100 mg, 137 mg, 150 mg, 200 mg, 250 mg, 274 mg, 300 mg, 350 mg, or 400 mg per day in one dose or divided doses. In another embodiment, the amantadine is administered orally.

In an embodiment, the second compound is levodopa. In another embodiment, the amount of levodopa may be administered at a dose of, for example, 250 mg-6000 mg per day in one or more divided doses. In another embodiment, the amount of Levodopa is 250 mg, 300 mg, 500 mg, 750 mg, 1,000 mg, 1,500 mg, 2,000 mg, 2,500 mg, 3,000 mg, 3,500 mg, 4,000 mg, 4,500 mg, 5,000 mg, 5,500 mg, or 6,000 mg per day in one dose or divided doses.

In one embodiment, the amount of pridopidine and the amount of the second compound are administered simultaneously. In another embodiment, the administration of the second compound substantially precedes the administration of pridopidine. In another embodiment, the administration of pridopidine substantially precedes the administration of the second compound. In another embodiment, the subject is receiving amantadine therapy or levodopa therapy prior to initiating pridopidine therapy. In another embodiment, the subject is receiving amantadine therapy or levodopa therapy for at least 24 weeks, 28 weeks, 48 weeks, or 52 weeks prior to initiating pridopidine therapy. In another embodiment, the subject is receiving pridopidine therapy prior to initiating receiving amantadine therapy or levodopa therapy. In another embodiment, the subject is receiving pridopidine therapy for at least 24 weeks, 28 weeks, 48 weeks, or 52 weeks prior to initiating receiving amantadine therapy or levodopa therapy.

In one embodiment, each of the amount of the second compound when taken alone and the amount of pridopidine when taken alone is effective to treat the subject. In another embodiment, either the amount of the second compound when taken alone, the amount of pridopidine when taken alone, or each such amount when taken alone is not effective to treat the subject. In another embodiment, either the amount of the second compound when taken alone, the amount of pridopidine when taken alone, or each such amount when taken alone is less effective to treat the subject.

In one embodiment, the pridopidine is administered adjunctively to the second compound. In other embodiments, the second compound is administered adjunctively to the pridopidine.

In an embodiment, a loading dose of an amount different from the intended dose is administered for a period of time at the start of the periodic administration. In another embodiment, the loading dose is double the amount of the intended dose. In another embodiment, the loading dose is half the amount of the intended dose.

This invention provides a method of treating a human subject afflicted with a levodopa induced dyskinesia comprising periodically administering to the subject an amount of levodopa and an amount of pridopidine, wherein the amounts when taken together are effective to treat the human subject.

In one embodiment, the levodopa induced dyskinesia is a peak dose dyskinesia. In another embodiment, the levodopa induced dyskinesia is diphasic dyskinesia.

In one embodiment, the amount of levodopa and the amount of pridopidine when taken together are effective to reduce a symptom of the levodopa induced dyskinesia in the human subject. In another embodiment, the symptom is abnormal movements, myoclonic jerks, irregular movements of extremities, gait, facial grimacing, ataxia, inability to sustain motor act, hand movement or balance. In another embodiment, the subject is afflicted with PD and the subject's motor function is assessed using the total motor score (TMS) or the modified motor score (mMS) derived from the Unified Parkinson's Disease Rating Scale (UPDRS). In yet another embodiment, the patient had an mMS score of 10 or greater at baseline. In another embodiment, the subject is afflicted with parkinsonism other than PD parkinsonism and the subject's motor function is assessed by the UDysRS.

In an embodiment of the present invention, the administration of levodopa and pridopidine improves a symptom of the levodopa induced dyskinesia by at least 10%. In an embodiment of the present invention, the administration of levodopa and pridopidine improves a symptom of the levodopa induced dyskinesia by at least 20%. In another embodiment, the administration of levodopa and pridopidine improves a symptom of the levodopa induced dyskinesia by at least 30%. In another embodiment, the administration of levodopa and pridopidine improves a symptom of the levodopa induced dyskinesia by at least 50%. In another embodiment, the administration of levodopa and pridopidine improves a symptom of the levodopa induced dyskinesia by more than 100%. In another embodiment, the administration of levodopa and pridopidine improves a symptom of the levodopa induced dyskinesia by more than 300%.

In one embodiment, the human subject is receiving levodopa therapy prior to initiating pridopidine therapy. In another embodiment, the administration of levodopa and/or amantadine precedes the administration of pridopidine by at least one week, at least one month, at least three months, at least six months, or at least one year.

In one embodiment, the levodopa is administered via oral administration. In another embodiment, the levodopa is administered daily. In another embodiment, the levodopa is administered more often than once daily. In another embodiment, the levodopa is administered less often than once daily.

In one embodiment, the amount of levodopa administered is about 50 mg to 8,000 mg/day. In one embodiment, pridopidine is administered orally. In another embodiment, pridopidine is administered through a nasal, inhalation, subcutaneous, intravenous, intraperitoneal, intramuscular, intranasal, buccal, vaginal, rectal, intraocular, intrathecal, topical or intradermal route. In another embodiment, the pridopidine is administered daily. In another embodiment, the pridopidine is administered more often than once daily. In another embodiment, the administration of pridopidine is administered twice a day. In another embodiment, the pridopidine is administered less often than once daily.

In embodiments for the treatment of LID or for the use in the treatment of LID, the amount of pridopidine administered is greater than 100 to 1000 mg/day. In another embodiment, the amount of pridopidine administered is between 45-400 mg/day. In another embodiment, the amount of pridopidine administered is 112.5-400 mg/day. In another embodiment, the amount of pridopidine administered is 180-400 mg/day. In another embodiment, the amount of pridopidine administered is 150-400 mg/day. In another embodiment, the amount of pridopidine administered is 150-350 mg/day. In another embodiment, the amount of pridopidine administered is 180-400 mg/day. In another embodiment, the amount of pridopidine administered is 200-400 mg/day. In another embodiment, the amount of pridopidine administered is 180 mg/day. In another embodiment, the amount of pridopidine administered is 200 mg/day. In another embodiment, the amount of pridopidine administered is 225 mg/day. In another embodiment, the amount of pridopidine administered is 250 mg/day. In another embodiment, the amount of pridopidine administered is 300 mg/day. In another embodiment, the amount of pridopidine administered is 350 mg/day. In another embodiment, the amount of pridopidine administered is 400 mg/day.

In embodiments for the treatment of DIMD other than LID or for the use in the treatment of DIMD other than LID, the amount of pridopidine administered is 10-1,000 mg/day. In another embodiment, the amount of pridopidine administered is 45-400 mg/day. In another embodiment, the amount of pridopidine administered is 20-180 mg/day. In another embodiment, the amount of pridopidine administered is 50-180 mg/day. In another embodiment, the amount of pridopidine administered is 30-120 mg/day. In another embodiment, the amount of pridopidine administered is 150-1000 mg/day. In another embodiment, the amount of pridopidine administered is 180-1000 mg/day. In another embodiment, the amount of pridopidine administered is 150-400 mg/day. In another embodiment, the amount of pridopidine administered is 150-350 mg/day. In another embodiment, the amount of pridopidine administered is 180 mg/day. In another embodiment, the amount of pridopidine administered is 90 mg/day. In another embodiment, the amount of pridopidine administered is about 45 mg/day. In another embodiment, the amount of pridopidine administered is about 90 mg/day. In one embodiment, the method further comprises administration of a second compound which is an antidepressant, a psychotropic drug, an antipsychotic, amisulpride, haloperidol, olanzapine, risperidone, sulpiride, or tiapride. In an embodiment, the periodic administration of the second compound and pridopidine continues for at least 3 days. In another embodiment, the periodic administration of the second compound and pridopidine continues for more than 30 days. In another embodiment, the periodic administration of the second compound and pridopidine continues for more than 42 days. In another embodiment, the periodic administration of the second compound and pridopidine continues for 8 weeks or more. In another embodiment, the periodic administration of the second compound and pridopidine continues for at least 12 weeks. In another embodiment, the periodic administration of the second compound and pridopidine continues for at least 24 weeks. In another embodiment, the periodic administration of the second compound and pridopidine continues for more than 24 weeks. In yet another embodiment, the periodic administration of the second compound and pridopidine continues for 6 months, or 12 months or more.

This invention also provides a package comprising (a) a first pharmaceutical composition comprising an amount of levodopa and a pharmaceutically acceptable carrier; (b) a second pharmaceutical composition comprising an amount of pridopidine and a pharmaceutically acceptable carrier; and optionally (c) instructions for use of the first and second pharmaceutical compositions together to treat a human subject afflicted with levodopa induced dyskinesia. In some embodiments the pridopidine is pridopidine HCl or other pharmaceutically acceptable salt.

In one embodiment of the package, the first pharmaceutical composition, the second pharmaceutical composition, or both the first and the second pharmaceutical composition are in tablet form. In one embodiment, the first pharmaceutical composition, the second pharmaceutical composition, or both the first and the second pharmaceutical composition are in the form of an aerosol or inhalable powder. In another embodiment, the first pharmaceutical composition, the second pharmaceutical composition, or both the first and the second pharmaceutical composition are in liquid form. In another embodiment, the first pharmaceutical composition, the second pharmaceutical composition, or both the first and the second pharmaceutical composition are in solid form. In another embodiment, the first pharmaceutical composition, the second pharmaceutical composition, or both the first and the second pharmaceutical composition are in capsule form.

In an embodiment of the package, the amount of pridopidine in the second composition is 45 to 400 mg. In another embodiment, the amount of pridopidine in the second composition is 75-400 mg. In another embodiment, the amount of pridopidine in the second composition is 90-400 mg. In another embodiment, the amount of pridopidine in the second composition is 112.5-400 mg. In another embodiment, the amount of pridopidine in the second composition is 150-350 mg. In another embodiment, the amount of pridopidine in the second composition is 180-400 mg. In another embodiment, the amount of pridopidine in the second composition is 225-400 mg. In another embodiment, the amount of pridopidine in the second composition is 45 mg. In another embodiment, the amount of pridopidine in the second composition is 75 mg. In another embodiment, the amount of pridopidine in the second composition is about 90 mg. In another embodiment, the amount of pridopidine in the second composition is about 112.5 mg. In another embodiment, the amount of pridopidine in the second composition is 125 mg. In another embodiment, the amount of pridopidine in the second composition is 150 mg.

In yet another embodiment, the amount of pridopidine in the second composition is 200 mg.

This invention also provides amantadine for use as an add-on therapy or in combination with pridopidine in treating a human subject afflicted with a neurodegenerative disorder.

This invention also provides a pharmaceutical composition comprising an amount of levodopa and/or amantadine and an amount of pridopidine. In one embodiment, the pharmaceutical composition is in the form of an aerosol or inhalable powder. In an embodiment, the pharmaceutical composition is in liquid form. In an embodiment, the pharmaceutical composition is in solid form. In an embodiment, the pharmaceutical composition is in capsule form. In an embodiment, the pharmaceutical composition is in tablet form.

In an embodiment of the present invention, the daily amount of pridopidine administered is greater than 100 mg and up to 400 mg. In another embodiment, the amount of pridopidine administered is 45-400 mg. In another embodiment, the amount of pridopidine administered is 110-400 mg. In another embodiment, the daily amount of pridopidine administered is 135-400 mg. In another embodiment, the daily amount of pridopidine administered is 250-400 mg. In another embodiment, the daily amount of pridopidine is 135-180 mg. In another embodiment, the daily amount of pridopidine administered is 180-350 mg. In another embodiment, the daily amount of pridopidine administered is 135 mg. In another embodiment, the daily amount of pridopidine administered is 180 mg. In another embodiment, the daily amount of pridopidine is 200 mg. In another embodiment, the daily amount of pridopidine administered is 225 mg. In another embodiment, the daily amount of pridopidine administered is 250 mg. In another embodiment, the daily amount of pridopidine administered is 300 mg. In another embodiment, the daily amount of pridopidine administered is 350 mg. In another embodiment, the daily amount of pridopidine administered is 400 mg. This invention also provides use of an amount of levodopa and/or amantadine and an amount of pridopidine in the preparation of a combination for treating a human subject afflicted with a levodopa induced dyskinesia wherein the levodopa and/or amantadine or pharmaceutically acceptable salt thereof and the pridopidine are administered simultaneously or contemporaneously.

This invention also provides a pharmaceutical composition comprising an amount of levodopa and/or amantadine for use in treating a subject afflicted with levodopa induced dyskinesia as an add-on therapy or in combination with pridopidine by periodically administering the pharmaceutical composition and the pridopidine to the subject.

This invention also provides a pharmaceutical composition comprising an amount of pridopidine for use treating a subject afflicted with levodopa induced dyskinesia as an add-on therapy or in combination with levodopa and/or amantadine by periodically administering the pharmaceutical composition and the levodopa and/or amantadine to the subject.

For the foregoing embodiments, each embodiment disclosed herein is contemplated as being applicable to each of the other disclosed embodiments. For instance, the elements recited in the method embodiments can be used in the pharmaceutical composition, package, and use embodiments described herein and vice versa.

All combinations, sub-combinations, and permutations of the various elements of the methods and uses described herein are envisaged and are within the scope of the invention.

Terms

As used herein, and unless stated otherwise, each of the following terms shall have the definition set forth below.

The articles "a", "an" and "the" are non-limiting. For example, "the method" includes the broadest definition of the meaning of the phrase, which can be more than one method.

As used herein, "effective" as in an amount effective to achieve an end means the quantity of a component that is sufficient to yield an indicated therapeutic response. For example, an amount effective to reduce a symptom of LID in a Parkinson's disease (PD) patient. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives. In a preferred embodiment, administration of an effective amount of a therapeutic compound is without undue adverse side effects (such as toxicity, irritation, or allergic response), commensurate with a reasonable benefit/risk ratio when used in the manner of this disclosure.

In some embodiments, compositions, uses and methods can be used to treat levodopa-induced dyskinesia (LID). LID can be present in PD patients who have been on levodopa for extended periods of time. 'Off-time' is when a PD patient's levodopa medication is no longer working well for them, and at least some of their Parkinson's symptoms have returned. The return of PD symptoms may include e.g.; slowness, stiffness or tremor; and sometimes total (akinesia) or partial (bradykinesia) immobility. 'On-time' is the time when a PD patient's levodopa medication is having benefit, and their Parkinson's symptoms are generally well controlled. Bad quality on-time is period of time when a PD patient's medication is not effective, for example, the patient is medicated and afflicted with disabling dyskinesia.

Three forms of dyskinesia have been classified on the basis of their course and presentation following treatment with levodopa; i) peak-dose dyskinesia (the most common form of LID; it correlates with high L-DOPA plasma level); ii) diphasic dyskinesia (occurs with rising and falling plasma levodopa levels; this form is usually dystonic or ballistic; does not respond to L-DOPA reduction); and iii) off-period dystonia (correlated to the akinesia that occurs before the full effect of L-DOPA sets in, when the plasma levels of L-DOPA are low) (Bargiotas 2013).

As used herein, to "treat" or "treating" encompasses reducing a symptom, inducing inhibition, regression, or stasis of the disorder and/or disease. As used herein, "inhibition" of disease progression or disease complication in a subject means preventing or reducing the disease progression and/or disease complication in the subject. In one embodiment "treating" or "treatment" refers to ameliorating at least one physical parameter, which may not be discernible by the subject. In yet another embodiment, "treating"" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Subject" includes humans. The terms "human," "patient," and "subject" are used interchangeably herein unless the context clearly indicates the contrary (e.g. in reference to healthy human volunteers). In an embodiment, the subject is a human adult. In an embodiment, the subject is a human adult having a mass of 70 kg.

"Administering to the subject" or "administering to the (human) patient" means the giving of, dispensing of, or application of medicines, drugs, or remedies to a subject/patient to relieve, cure, or reduce the symptoms associated with a condition, e.g., a pathological condition. Oral administration is one way of administering the instant compounds to the subject. The administration can be periodic administration.

As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times a week and so on, etc.

As used herein, "adjunctively" means treatment with or administration of an additional compound, with a primary compound, for example for increasing the efficacy or safety of the primary compound or for facilitating its activity.

As used herein, "pridopidine" means pridopidine base or a pharmaceutically acceptable salt thereof, as well as its analogues or combination of pridopidine and its analogues or derivatives, for example deuterium-enriched version of pridopidine and salts. Examples of deuterium-enriched pridopidine and salts and their methods of preparation may be found in U.S. Application Publication Nos. 2013-0197031, 2016-0166559 and 2016-0095847, the entire content of each of which is hereby incorporated by reference. Examples of acid addition salts of pridopidine include, but is not limited to, the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. In certain embodiments, pridopidine is a pharmaceutically acceptable salt, such as the HCl salt or tartrate salt. Preferably, in any embodiments of the invention as described herein, the pridopidine is in the form of its hydrochloride salt.

In one embodiment, the analogues of pridopidine are represented by the following structures:

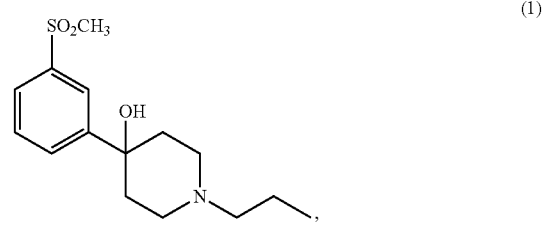

(1)

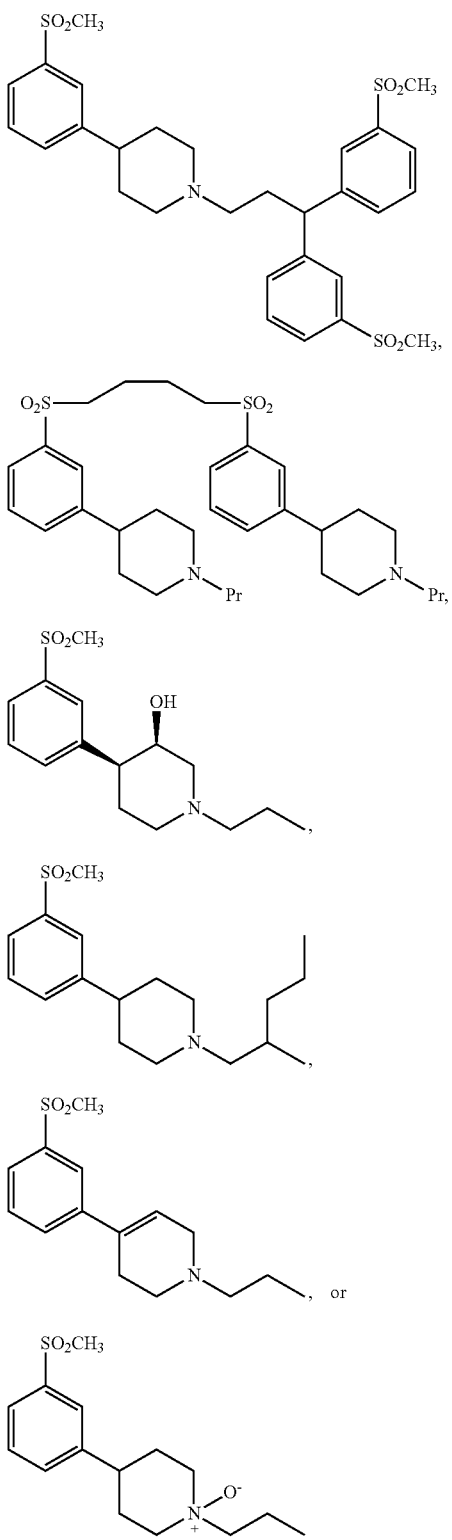

Preferably, in any embodiments of the invention as described herein, the pridopidine is in the form of its hydrochloride salt. Pridopidine mixtures, compositions, the process for the manufacture thereof, the use thereof for treatment of various conditions, and the corresponding dosages and regimens are described in, e.g., PCT International Application Publication Nos. WO 2001/46145, WO 2011/107583, WO 2006/040155, U.S. Patent Application Publication No. 2011/0206782, U.S. Patent Application Publication No. 2010/0197712, the entire content of each of which is hereby incorporated by reference.

As used herein, an "amount" or "dose" of pridopidine as measured in milligrams refers to the milligrams of underivatized pridopidine base present in a preparation, dose or daily dose, regardless of the form of the preparation. A "dose of 200 mg pridopidine" means the amount of pridopidine in a preparation is sufficient to provide 200 mg of underivatized pridopidine base having a naturally occurring isotope distribution, regardless of the form of the preparation. Thus, when in the form of a salt, e.g. a pridopidine hydrochloride, the mass of the salt form necessary to provide a dose of 200 mg underivatized pridopidine base would be greater than 200 mg due to the presence of the additional salt ion. Similarly, when in the form of a deuterium-enriched derivative, the mass of the derivatized form necessary to provide a dose of 200 mg underivatized pridopidine base having a naturally occurring isotope distribution would be greater than 200 mg due to the presence of the additional deuterium. To exemplify, the factor for converting mass of pridopidine HCl to mass of pridopidine base is 0.885 (e.g. 1 mg pridopidine HCl×0.885 mg pridopidine base). Accordingly, 112.99 mg/day dose of pridopidine HCl is equivalent to a 100 mg dose of pridopidine base.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1; 0.2 . . . 0.9; and 1, 2 . . . 49 mg unit amounts are included as embodiments of this invention. By any range of time disclosed herein (i.e. weeks, months, or years), it is meant that all lengths of time of days and/or weeks within the range are specifically disclosed as part of the invention. Thus, for example, 3-6 months means that 3 months and 1 day, 3 months and 1 week, and 4 months are included as embodiments of the invention.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination. Further, reference to values stated in ranges includes each and every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

As used herein, "levodopa" means L-3,4-dihydroxyphenylalanine (levodopa or L-DOPA) levodopa or a pharmaceutically acceptable salt thereof, as well as derivatives.

As used herein, the term "C max" refers to the maximum plasma, serum or blood concentration of a drug, following administration of the drug, e.g. pridopidine, or a pharmaceutically acceptable salt thereof.

As used herein, the term "C min" refers to the minimum plasma, serum or blood concentration of a drug, following administration of the drug, e.g. pridopidine, or a pharmaceutically acceptable salt thereof.

As used herein, the term "T max" refers to the time required to reach the maximal plasma, serum or blood concentration ("C max") of the drug, following administration of the drug, e.g. pridopidine, or a pharmaceutically acceptable salt thereof.

As used herein, the term "AUC" refers to the area under the plasma, serum or blood concentration versus time curve. "AUC0-t" refers to the area under the plasma, serum or blood concentration versus time curve wherein t (hours) is the last measured time point. "AUCinfinity" refers to the area under the plasma, serum or blood concentration versus time curve extrapolated to infinity. $AUC_{24,ss}$ refers to area under the concentration-time curve from 0 to 24 hours at steady state. Units are presented as h*ng/ml.

Pharmaceutically Acceptable Salts

The active compounds for use according to the invention may be provided in any form suitable for the intended administration. Suitable forms include pharmaceutically acceptable salts, and pre- or prodrug forms of the compound of the invention.

A "salt thereof" is a salt of the instant compound which has been modified by making acid or base salts of the compound. The term "pharmaceutically acceptable salt" in this respect, refers to the relatively non-toxic, inorganic and organic acid or base addition salts of compound of the present invention suitable for pharmaceutical use. Pharmaceutically acceptable salts may be formed by procedures well known and described in the art. One means of preparing such a salt is by treating a compound of the present invention with an inorganic base.

Examples of pharmaceutically acceptable addition salts include, without limitation, the non-toxic inorganic and organic acid addition salts such as the hydrochloride, the hydrobromide, the L-tartrate, the nitrate, the perchlorate, the phosphate, the sulphate, the formate, the acetate, the aconate, the ascorbate, the benzene-sulphonate, the benzoate, the cinnamate, the citrate, the embonate, the enantate, the fumarate, the glutamate, the glycolate, the lactate, the maleate, the malonate, the mandelate, the methane-sulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art. In certain embodiments, pridopidine is provided as a pharmaceutically acceptable salt, such as the HCl salt or tartrate salt. Preferably, in any embodiments of the invention as described herein, the pridopidine is in the form of its hydrochloride salt. "Deuterium-enriched" means that the abundance of deuterium at any relevant site of the compound is more than the abundance of deuterium naturally occurring at that site in an amount of the compound. The naturally occurring distribution of deuterium is about 0.0156%. Thus, in a "deuterium-enriched" compound, the abundance of deuterium at any of its relevant sites is more than 0.0156% and can range from more than 0.0156% to 100%, for example 50%, 60%, 70%, 75%, 8-%, 85%, 90%, 95%, 98% or 100%. Deuterium-enriched compounds may be obtained by exchanging hydrogen with deuterium or synthesizing the compound with deuterium-enriched starting materials. In some embodiments, the methods, uses, packages and kits include deuterated pridopidine.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection, for example infusion. The pharmaceutical composition of the invention can be manufactured by the skilled person by use of standard methods and conventional techniques appropriate to the desired formulation. When desired, compositions adapted to give sustained release of the active ingredient may be employed.

Add-On/Combination Therapy

When the invention comprises a combination of the active compound and an additional one, or more, therapeutic and/or prophylactic ingredients, the combination of the invention may be formulated for its simultaneous or contemporaneous administration, with at least a pharmaceutically acceptable carrier, additive, adjuvant or vehicle. This has the implication that the combination of two or three or more active compounds may be administered:

as a combination that is part of the same medicament formulation, the two or more active compounds being then administered simultaneously, or as a combination of two or more units, each with one of the active substances giving rise to the possibility of simultaneous, or contemporaneous administration.

In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry, 1999).

Not only may the interaction between two drugs affect the intended therapeutic activity of each drug, but the interaction may increase the levels of toxic metabolites (Guidance for Industry, 1999). The interaction may also heighten or lessen the side effects of each drug. Hence, upon administration of two drugs to treat a disease, it is unpredictable what change will occur in the negative side profile of each drug.

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs (Guidance for Industry 1999).

In one example, combined administration of glatiramer acetate (GA) and interferon (IFN) has been experimentally shown to abrogate the clinical effectiveness of either therapy. (Brod 2000). In another experiment, it was reported that the addition of prednisone in combination therapy with IFN-β antagonized its up-regulator effect. Thus, when two drugs are administered to treat the same condition, it is unpredictable whether each will complement, have no effect on, or interfere with, the therapeutic activity of the other in a human subject.

Therefore, the state of the art at the time of filing is that the effects of an add-on or combination therapy of two drugs, in particular levodopa and pridopidine or amantadine and pridopidine, could not have been predicted until the results of a formal combination study were available.

As used herein, "combination" means an assemblage of reagents for use in therapy either by simultaneous or contemporaneous administration. Simultaneous administration refers to administration of an admixture (whether a true mixture, a suspension, an emulsion or other physical combination) of pridopidine and a second compound (for example, levodopa, amantadine or combination of levodopa and amantadine). In this case, the combination may be the admixture or separate containers of pridopidine the second compound that are combined just prior to administration. Contemporaneous administration, or concomitant administration refers to the separate administration of pridopidine and the second compound at the same time, or at times sufficiently close together that a synergistic activity relative to the activity of either pridopidine alone the second compound alone is observed or in close enough temporal proximately to allow the individual therapeutic effects of each agent to overlap.

As used herein, "add-on" or "add-on therapy" means a therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time. For example, adding pridopidine or pridopidine and amantadine therapy to a Parkinson's disease patient already receiving levodopa therapy. The FDA has recently approved extended release amantadine (Gocovri™; previously ADS-5102) for treating LID in patients with Parkinson's disease.

As used herein, "amantadine" means amantadine or a pharmaceutically acceptable salt thereof, as well as derivatives, for example deuterium-enriched version of amantadine and salts. Amantadine is descried in Prescribers' Digital Reference which is hereby incorporated by reference (for example, Amantadine PDR 2017). Amantadine as used herein refers to amantadine base or any pharmaceutically acceptable salt thereof.

In one example, an extended release formulation of amantadine may be administered to the subject in the evening and pridopidine may be given twice or three times during the day, for example morning and afternoon. In one example, immediate release formulations of amantadine are administered in the morning and afternoon and pridopidine is administered in the morning, afternoon and early evening. Optionally, levodopa is administered to the subject.

Parkinson's disease (PD) is a progressive disorder of the nervous system that affects movement. PD is the second most common progressive neurodegenerative disorder affecting older American adults and is predicted to increase in prevalence as the United States population ages. The disease is a result of pathophysiologic loss or degeneration of dopaminergic neurons in the substantia nigra (SN) of the midbrain and the development of neuronal Lewy Bodies. PD is characterized by both motor and non-motor symptoms. PD patients classically display rest tremor, rigidity, bradykinesia, and stooping posture, but can also exhibit neurobehavioral disorders (depression, anxiety), cognitive impairment (dementia), and autonomic dysfunction (e.g., orthostasis and hyperhidrosis). The underlying molecular pathogenesis involves multiple pathways and mechanisms: α-synuclein proteostasis, mitochondrial function, oxidative stress, calcium homeostasis, axonal transport and neuroinflammation. Dyskinesia refers to hyperkinetic movement disorders in which a variety of abnormal involuntary movements can manifest as single or multiple phenomenologies, which are typically present during wakefulness and cease during sleep.

Along with rigidity and bradykinesia, certain types of dyskinesia, e.g. tremor, can be a feature that is associated with PD and that differentiates PD from other disorders, where they are much less common. Dyskinesia and other features of PD are measured as part of the Unified Parkinson's Disease Rating Scale (UPDRS) (Goetz 2007; Movement Disorder Society Task Force 2003; the entire contents of which are hereby incorporated by reference).

The dopamine (DA) precursor L-DOPA (also known as levodopa) has been the most effective treatment for PD for over 40 years, however the response to this treatment changes with disease progression and most patients develop dyskinesias and motor fluctuations, resulting from L-DOPA, within a few years of therapy.

The symptoms of PD are most commonly treated with levodopa. However, use of levodopa is often complicated with dyskinesia that is caused by levodopa, mitigating its beneficial effects. The features of Levodopa-Induced Dyskinesia (LID) are different from those of PD dyskinesia and include chorea, dystonia, akathisia, athetosis and tics. Dyskinesia in PD can sometimes, in a general sense, refer to the movement disorder associated with PD. LID, on the other hand, is related to administration of L-DOPA and incorporates chorea, dystonia, akathisia, athetosis, tics, myoclonus. Akathisia and dystonia are not seen in PD patients not treated with L-DOPA. These specific dyskinetic features of LID are measured by the Unified Dyskinesia Rating Scale (UDysRS). The UDysRS, having both subjective and objective dyskinesia ratings, rate all aspects of LID including features such as chorea and dystonic movements (Goetz 2013, the entire contents of which are hereby incorporated by reference).

The mechanisms underlying development of LID involve interplay between progressive degeneration of neurons in the basal ganglia and chronic dopaminergic stimulation by levodopa treatment. Mechanisms underlying LID are not completely understood, however both pre- and postsynaptic disturbances of dopamine (DA) transmission are involved. Presynaptic factors contribute to generating fluctuating levels of levodopa and DA in the brain and include loss of Dopamine Transporters (DAT) and loss of physiological DA storage and release sites. Postsynaptic molecular mechanisms include changes in dopamine receptor trafficking, signaling and supersensitivity, structural and molecular changes in striatal neurons and altered activity in the basal ganglia. Non-dopaminergic modulatory systems such as the glutamatergic system, serotonergic neurons as well as other neuromodulators (Noradrenaline, acetylcholine, opioids and cannabinoids) also play a role in LID. Additional functional and structural changes involved in the pathogenesis of dyskinesia include modulation of vascular endothelial growth factor expression level by astrocytes and over activation of the adenosine A2A receptors. Changes in the extracellular levels of glutamate and altered levels of the glutamate transporter gene expression have been observed in basal ganglia structure of dyskinetic animals. Taken together, these functional alterations point towards a complex multi factorial mechanism behind the generation and expression of dyskinesia which could explain the difficulty of managing these motor complications (reviewed in Daneault 2013).

LID is the most common cause of medication-induced movement disorder. However, drug-induced movement disorders (DIMDs) can be elicited by several kinds of pharmaceutical agents which modulate dopamine neurotransmission as well as other neurotransmission in the central nervous system such as serotonin, adrenaline and acetylcholine. The major groups of drugs responsible for DIMDs include antidepressants, antipsychotics (neuroleptics), antiepileptics, antimicrobials, antiarrhythmics, mood stabilizers and gastrointestinal drugs among others. These movement disorders can include: Parkinsonism, Tardive dyskinesia, Chorea, Dystonia, Tremor, Akathisia, Myoclonus or Tics. The term "Parkinson's disease levodopa-induced dyskinesia;" "levodopa-induced dyskinesia," or "LID" refers to an abnormal muscular activity disorder that results from levodopa therapy, the disorder being characterized by either disordered or excessive movement (referred to as "hyperkinesia" or "dyskinesia"), slowness, or a lack of movement (referred to as "hypokinesia," "bradykinesia," or "akinesia"). LID includes any involuntary movement that results from levodopa therapy, such as chorea, ballism, dystonia, athetosis, tic, or myoclonus. The most common types of levodopa-induced dyskinesia are chorea and dystonia, which often coexist. (Johnston 2001). Based on their relationship with levodopa dosing, levodopa-induced dyskinesias are classified as peak-dose, diphasic, off state, on state, and yo yo dyskinesias. Peak-dose dyskinesias are the most common forms of LID and are related to peak plasma (and possibly high striatal) levels of levodopa. They involve the head, trunk, and limbs, and sometimes respiratory muscles. Dose reduction can ameliorate them, frequently at the cost of deterioration of parkinsonism. Peak-dose dyskinesias are usually choreiform, though in the later stages dystonia can superimpose. Diphasic dyskinesias develop when plasma levodopa levels are rising or falling, but not with the peak levels. They are also called D-I-D (dyskinesia-improvement-dyskinesia). D-I-D are commonly dystonic in nature, though chorea or mixed pattern may occur. They do not respond to levodopa dose reduction and may rather improve with high dose of levodopa. "Off" state dystonias occur when plasma levodopa levels are low (for example, in the morning). They are usually pure dystonia occurring as painful spasms in one foot. They respond to levodopa therapy. Rare forms of LID include "on" state dystonias (occurring during higher levels of levodopa) and yo-yo dyskinesia (completely unpredictable pattern).

Other Drug-Induced Movement Disorders (DIMD)

Drug-induced dystonia is a twisting movement or abnormal posture (or a combination thereof) may manifest as acute or tardive involuntary limb movements, facial grimacing, cervical dystonia, oculogyric crisis, rhythmic tongue protrusion, jaw opening or closing, spasmodic dysphonia, and, rarely, stridor and dyspnea.

Drug-induced tardive dyskinesia includes involuntary movements that resemble multiple movement disorders. The term tardive means "late" to indicate that the condition occurs sometime after drug exposure, and the terms dyskinesia and dystonia describe the types of movements involved. Although the pathophysiologic mechanism of TD is unknown, it is believed that prolonged administration of neuroleptics, which act by blocking dopamine receptors (e.g., amoxapine, chlorpromazine, fluphenazine, haloperidol, one notable exception being clozapine), results in hypersensitivity or up-regulation of dopamine receptors in the basal ganglia of the brain (see e.g., Andrews, Can J Psych 39:576). Drugs that increase or enhance the dopamine response, especially indirect dopamine agonists, can aggravate the disorder and the use of such drugs in neuroleptic therapy is typically avoided. (Bezchibnyk-Butler & Remington, Can J. Psych. 39:74, 1994).

Drug-induced akathisia (restlessness and characteristic movements of the legs) is one of the most disagreeable extrapyramidal side effects often caused by use of antipsychotic and antidepressant drugs.

Drug-induced Tourette syndrome (TS) is a neurological disorder with repetitive, involuntary movements or vocalizations. These involuntary movements are known as tics. Some of the most common tics are eye blinking, among other eye movements and facial grimacing, shoulder shrugging, and head or shoulder jerking. Some of these can be combined with one another to make more complex tics. Some tics involve self-harm but only in a small percentage (10% to 15%) of individuals Non-limiting examples of drugs that can induce movement disorders (DIMD) include any one of (US trade name in parentheses): acetohenazine (Tindal), amoxapine (Asendin), chlorpromazine (Thorazine), fluphenazine (Permitil, Prolixin), haloperidol (Haldol), loxapine (Loxitane, Daxolin), mesoridazine (Serentil), metaclopramide (Reglan), molinndone (Lindone, Moban), perphanzine (Trilafrom, Triavil), piperacetazine (Quide), prochlorperzine (Compazine, Combid), promazine (Sparine), promethazine (Phenergan), thiethylperazine (Torecan), thioridazine (Mellaril), thiothixene (Navane), trifluoperazine (Stelazine), triflupromazine (Vesprin), and trimeprazine (Temaril).

As used herein, "effective" when referring to an amount of pridopidine (or pridopidine and a second compound) refers to the quantity of pridopidine (or the quantities of pridopidine and a second compound) that is sufficient to yield a desired therapeutic response.

In some embodiments, pridopidine is administered with acetophenazine (Tindal). In some embodiments, pridopidine is administered with amoxapine (Asendin). In some embodiments, pridopidine is administered with chlorpromazine (Thorazine). In some embodiments, pridopidine is administered with fluphenazine (Permitil, Prolixin). In some embodiments, pridopidine is administered with haloperidol (Haldol). In some embodiments, pridopidine is administered with loxapine (Loxitane, Daxolin). In some embodiments, pridopidine is administered with mesoridazine (Serentil). In some embodiments, pridopidine is administered with metaclopramide (Reglan). In some embodiments, pridopidine is administered with molinndone (Lindone, Moban). In some embodiments, pridopidine is administered with perphanzine (Trilafrom. Triavil). In some embodiments, pridopidine is administered with piperacetazine (Quide). In some embodiments, pridopidine is administered with prochlorperzine (Compazine, Combid). In some embodiments, pridopidine is administered with promazine (Sparine). In some embodiments, pridopidine is administered with promethazine (Phenergan). In some embodiments, pridopidine is administered with thiethylperazine (Torecan). In some embodiments, pridopidine is administered with thioridazine (Mellaril). In some embodiments, pridopidine is administered with thiothixene (Navane). In some embodiments, pridopidine is administered with trifluoperazine (Stelazine). In some embodiments, pridopidine is administered with triflupromazine (Vesprin). In some embodiments, pridopidine is administered with trimeprazine (Temaril).

Parkinson's Disease Rating Scales

Several rating scales have been developed to measure involuntary movements in subjects afflicted with movement disorders, including parkinsonism, and PD patients. For example, the Unified Dyskinesia Rating Scale (UDysRS) was developed to evaluate involuntary movements often associated with treated Parkinson's disease. (Unified Dyskinesia Rating Scale (UDysRS), 2008, the entire content of which is hereby incorporated by reference). The UDysRS measures the intensity of dyskinesias in different body areas, the degree of impairment caused by dyskinesias when patients perform tasks of daily living, and the patient's perception of disability from dyskinesias. There are two primary sections:

Historical [Part 1 (On-Dyskinesia) and Part 2 (Off-Dystonia)]

Objective [Part 3 (Impairment) and Part 4 (Disability)]

On-Dyskinesia refers to the choreic and dystonic movements described to the patient as "jerking or twisting movements that occur when your medicine is working."

Off-Dystonia is described to the patient as "spasms or cramps that can be painful and occur when Parkinson's disease medications are not taken or are not working".

The MDS-UPDRS, Movement Disorder Society-Sponsored revision of the Unified Parkinson's Disease Rating Scale is another example of a rating scale often used in evaluating a PD patient's symptoms pre and post treatment (Goetz, 2008a; the entire content of which is hereby incorporated by reference).

The Total Unified Parkinson's Disease Rating Scale (UPDRS) score represents the level or severity of Parkinson's disease symptoms. It is used for measuring the change from baseline in efficacy variables during the treatment. UPDRS consists of a four-part test. A total of 42 items are included in Parts I-IV. Each item in parts I-III receives a score ranging from 0 to 4 where 0 represents the absence of impairment and 4 represents the highest degree of impairment. The sum of Parts I-IV at each study visit provides a Total UPDRS score. Parts I, II and IV are historical information. Part I is designed to rate mentation, behavior and mood (items 1-4). Part II (items 5-17) relates to Activities of Daily Living and refers to speech, swallowing, handwriting and the like. Part III (items 18-31) is a motor examination at the time of a visit and relates to facial expressions, tremor, rigidity and the like. Part IV (Items 32-42) relates to complications of the therapy and include questions relating to the disability and pain of the dyskinesia, on-off periods and the like.

The following measures may be used to assess efficacy of pridopidine in treating DIMD: change in Abnormal Involuntary Movement Scale (AIMS) score (items 1 through 7) from baseline to end of long-term therapy (Week 54) as assessed by blinded central video rating; proportion of subjects who are a treatment success at the end of long-term therapy (Week 54), based on the Clinical Global Impression of Change (CGIC) (in which a treatment success is defined as Much or Very Much Improved); change in the modified Craniocervical Dystonia (CDQ-24) score from baseline of this study to the end of long-term therapy (Week 54); proportion of subjects who have a 50% or greater reduction in AIMS score from baseline of this study to the end of long term therapy (Week 54); proportion of subjects who are a treatment success at the end of long-term therapy (Week 54), based on the Patient Global Impression of Change (PGIC) (in which a treatment success is defined as Much or Very Much Improved); percent change in AIMS score from Baseline of this study to the end of long term therapy (Week 54); and based on the change in AIMS score from baseline of this study to the end of long-term therapy (Week 54), as assessed by blinded central video rating, the cumulative proportion of responders ranging from a 10% improvement from baseline to a 90% improvement from baseline in steps of 10 percentage points. The Hauser PD diary is a valuable tool to assess on/off time in PD patients (Hauser 2004), including ON time with dyskinesia.

Rating scales including UPDRS, AIMS and UDysRS are available, for example, through the International Parkinson and Movement Disorder Society globally and from persons skilled in the art of movement disorder.

For all studies, the patient and independent rater may be independently blinded or not blinded. In some embodiment, patient and rater are blinded.

A "symptom" associated with a levodopa induced dyskinesia includes any clinical or laboratory manifestation associated with the levodopa induced dyskinesia and is not limited to what the subject can feel or observe. For example, a symptom of LID includes, but is not limited to involuntary movement, such as chorea, ballism, dystonia, tic, or myoclonus. The subject may experience one or more of the symptoms. For example, chorea and dystonia often coexist. Other symptoms may become apparent including tics or stereotypy.

"Improvement of" or "improving" or "ameliorating" a symptom as used herein refers to a favorable change in the patient's symptom as compared to baseline or as compared to a control subject not receiving the treatment. As used herein, "substantially precedes administration" means that the administration of one agent precedes another agent; and the two agents are not administered simultaneously or contemporaneously.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

It is understood that where a parameter range is provided, all integers within that range, and tenths thereof, are also provided by the invention. For example, "0.1-2.5 mg/day" includes 0.1 mg/day, 0.2 mg/day, 0.3 mg/day, etc. up to 2.5 mg/day.

The following numbered clauses define various aspects and features of the present invention:

1. A method of treating a subject afflicted with a drug-induced movement disorder (DIMD) comprising periodically administering to the subject an amount of pridopidine effective to treat the subject.

2. The method of clause 1, wherein the DIMD comprises dyskinesia.

3. The method of clause 2, wherein the dyskinesia is levodopa-induced dyskinesia (LID).

4. The method of clause 3, wherein treating comprises reducing a side effect of levodopa.

5. The method of clause 3, wherein the subject is a Parkinson's disease patient.

6. The method of clause 5, wherein the subject is an advanced stage Parkinson's disease patient.

7. The method of any one of clauses 3-6, wherein the subject is concurrently being treated with levodopa.

8. The method of clause 7, wherein the amount of pridopidine and the levodopa are administered simultaneously.

9. The method of clause 7, wherein the amount of pridopidine and the levodopa are co-formulated.

10. The method of clause 7, wherein the amount of pridopidine and the levodopa are administered sequentially and in separate pharmaceutical formulations.

11. The method of any one of clauses 3-10, wherein the amount of pridopidine is effective to alleviate or reduce a symptom associated with the levodopa treatment.

12. The method of clause 11, wherein the symptom is abnormal movements, myoclonic jerks, irregular movements of extremities, gait, facial grimacing, ataxia, inability to sustain motor act, hand movement or balance.

13. The method of clause 11, wherein the symptom is choreiform peak dose dyskinesia, or dystonic peak dose dyskinesia.

14. The method of clause 11, wherein the symptom is bad quality on-time evoked by levodopa.

15. The method of clause 11-14, wherein the administration of pridopidine improves the symptom of the levodopa induced dyskinesia by at least 8%, 10%, 20%, by at least 30% or by at least 50%.

16. The method of any one of clauses 3-15, wherein the anti-parkinsonian effect of levodopa is not affected by the amount of pridopidine.

17. The method of clause 1, wherein the DIMD is induced by a drug selected from an antidepressant, an antipsychotic, an antiepileptic, an antimicrobial, an antiarrhythmic, a mood stabilizer, a gastrointestinal drug or any combination thereof.

18. The method of clause 17, wherein the DIMD is selected from parkinsonism, tardive dyskinesia, chorea, dystonia, tremor, akathisia, athetosis, myoclonus or tics.

19. The method of clause 18, wherein the DIMD is Tardive dyskinesia.

20. The method of clause 18, wherein the DIMD is drug-induced dystonia.

21. The method of any one of clauses 2-16 and 19, wherein the dyskinesia in the subject is assessed by the UDysRS or UPDRS.

22. The method of clause 21, wherein the patient had a UDysRS score or UPDRS score of 10 or greater at baseline.

23. The method of any one of clauses 1-22 wherein the amount of pridopidine is administered via oral administration.

24. The method of any one of clauses 1-23, wherein the amount of pridopidine is administered once daily.

25. The method of any one of clauses 1-23, wherein the amount of pridopidine is administered twice daily or three times daily.

26. The method of any one of clauses 1-25, wherein the pridopidine is in form of base or in form of salt.

27. The method of clause 26, wherein the pridopidine salt is pridopidine hydrochloride.

28. The method clause 1-27, wherein the amount of pridopidine administered is greater than the equivalent of 100 mg pridopidine HCl per day.

29. The method of clause 28, wherein the amount of pridopidine administered is greater than 100 mg/day to 400 mg/day.

30. The method of any one of clauses 1-29, wherein the amount of pridopidine is 135 mg/day, 180 mg/day, 225 mg/day, 300 mg/day, 350 mg/day, or 400 mg/day.

31. The method of any one of clauses 1-29, wherein the amount of pridopidine administered is from 135 mg per day to 225 mg per day.

32. The method of clause 28, wherein the amount of pridopidine administered is from 45 mg per day to 180 mg per day, from 135 mg per day to 400 mg per day or 150 mg per day to 300 mg per day.

33. The method of clause 28, wherein the amount of pridopidine administered is 22.5 mg, 45 mg, 67.5, mg, 90 mg, 100 mg, 112.5 mg, 125 mg, 135 mg, 150 mg, 180 mg per day, 225 mg/day, 250 mg/day, 270 mg/day, 275 mg/day, 300 mg/day, 350 mg/day, 360 mg/day, 375 mg/day or 400 mg/day.

34. The method of any one of clauses 3-16 or 21-33, further comprising administering to the subject a therapeutically effective amount of a second compound, wherein the second compound is levodopa, amantadine or a combination of levodopa and amantadine, or wherein the second compound is an analog of pridopidine of the following or a combination thereof:

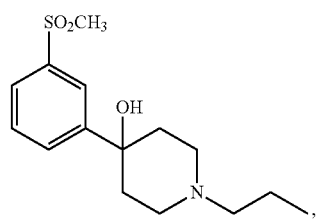
(1)

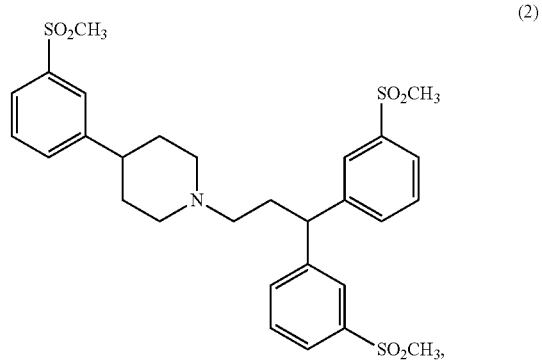
(2)

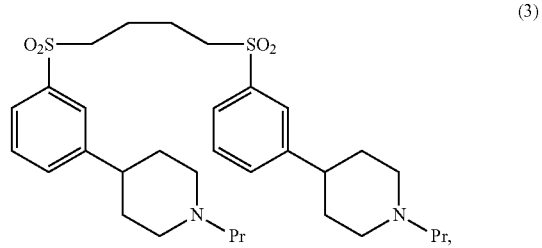
(3)

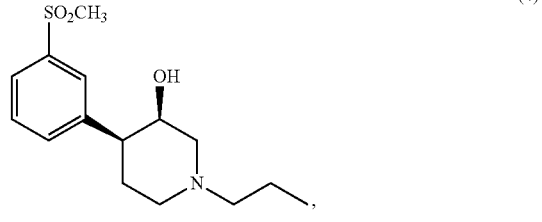
(4)

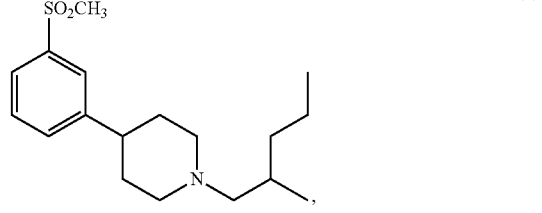
(5)

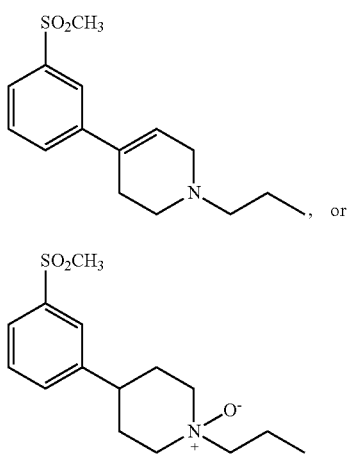

35. The method of clause 34, wherein the pridopidine and the second compound are administered in one unit.

36. The method of clauses 34, wherein the pridopidine and the second compound are administered in more than one unit.

37. The method of any one of clauses 34-36, wherein the second compound is amantadine.

38. The method of any one of clauses 34-36, wherein the amount of amantadine is 10-400 mg.

39. The method of any one of clauses 34-36, wherein the amount of amantadine is 10, 50, 100, 137, 150, 200, 250, 274, 300, 350, or 400 mg.

40. The method of any one of clauses 34-39, wherein the amantadine is administered orally.

41. The method of any one of clauses 34-40, wherein the second compound is levodopa.

42. The method of any one of clauses 34-41, wherein the amount of pridopidine and the amount of the second compound are administered simultaneously.

43. The method of any one of clauses 34-41, wherein the administration of the second compound substantially precedes the administration of pridopidine.

44. The method of any one of clauses 34-41, wherein the administration of pridopidine substantially precedes the administration of the second compound.

45. The method of any one of clauses 34-41, wherein the subject is receiving second compound therapy prior to initiating pridopidine therapy.

46. The method of clause 45, wherein the subject is receiving second compound therapy for at least 24 weeks, 28 weeks, 48 weeks, or 52 weeks prior to initiating pridopidine therapy.

47. The method of any one of clauses 34-44, wherein the subject is receiving pridopidine therapy prior to initiating receiving amantadine therapy.

48. The method of clause 47, wherein the subject is receiving pridopidine therapy for at least 24 weeks, 28 weeks, 48 weeks, or 52 weeks prior to initiating receiving amantadine therapy.

49. The method of any one of clauses 34-48, wherein each of the amount of the second compound when taken alone, and the amount of pridopidine when taken alone is effective to treat the subject.

50. The method of any one of clauses 34-48, wherein either the amount of the second compound when taken alone, the amount of pridopidine when taken alone, or each such amount when taken alone is not effective to treat the subject.

51. The method of any one of clauses 34-48, wherein either the amount of the second compound when taken alone, the amount of pridopidine when taken alone, or each such amount when taken alone is less effective to treat the subject.

52. The method of any one of clauses 34-48, wherein the pridopidine is administered adjunctively to the second compound.

53. The method of any one of clauses 34-48, wherein the second compound is administered adjunctively to the pridopidine.

54. The method of any one of clauses 1-53, wherein a loading dose of an amount different from the intended dose is administered for a period of time at the start of the periodic administration.

55. A pharmaceutical composition comprising an effective amount of pridopidine for use in treating a subject afflicted with a drug-induced movement disorder (DIMD).

56. Use of an amount of pridopidine for the manufacture of a medicament for use in treating a subject afflicted with a drug-induced movement disorder (DIMD).

57. A package comprising:
a) a pharmaceutical composition comprising an amount of pridopidine; and optionally
b) instructions for use of the pharmaceutical composition to treat a subject afflicted with a drug-induced movement disorder (DIMD).

58. A therapeutic package for dispensing to, or for use in dispensing to, a subject, which comprises:
a) one or more unit doses, each such unit dose comprising an amount of pridopidine thereof, wherein the amount of said pridopidine in said unit dose is effective, upon administration to said subject, to treat a drug-induced movement disorder (DIMD) in the subject, and
b) a finished pharmaceutical container therefor, said container containing said unit dose or unit doses, said container further containing or comprising labeling directing the use of said package in the treatment of a subject afflicted with the DIMD.

59. A package comprising:
a) a first pharmaceutical composition comprising an amount of pridopidine and a pharmaceutically acceptable carrier;
b) a second pharmaceutical composition comprising an amount of a second compound and a pharmaceutically acceptable carrier; and optionally
c) instructions for use of the first and second pharmaceutical compositions together to treat a subject afflicted with a drug-induced movement disorder (DIMD).

60. The package of clause 59, wherein the amount of the second compound and the amount of pridopidine are prepared to be administered simultaneously, contemporaneously or concomitantly.

61. A therapeutic package for dispensing to, or for use in dispensing to, a subject afflicted with a drug-induced movement disorder (DIMD), which comprises:
a) one or more unit doses, each such unit dose comprising:
i) an amount of pridopidine and
ii) an amount of a second compound;
wherein the respective amounts of said pridopidine and the second compound in said unit dose are effective, upon concomitant administration to said subject, to treat the subject, and b) a finished pharmaceutical container therefor, said container containing said unit dose or unit doses, said container further containing or comprising labeling directing the use of said package in the treatment of said subject.

62. A pharmaceutical composition comprising an amount of pridopidine and an amount of amantadine.

63. The pharmaceutical composition of clause 62 for use in treating a subject afflicted with a drug-induced movement disorder (DIMD), wherein the pridopidine and the amantadine are prepared to be administered simultaneously, contemporaneously or concomitantly.

64. A pharmaceutical composition in unit dosage form, useful in treating a subject afflicted with a drug-induced movement disorder (DIMD), which comprises:
   a) an amount of pridopidine;
   b) an amount of second compound;
wherein the respective amounts of amantadine and said pridopidine in said composition are effective, upon concomitant administration to said subject of one or more of said unit dosage forms of said composition, to treat the subject.

65. A pharmaceutical composition comprising an amount of pridopidine for use in treating a subject afflicted with a drug-induced movement disorder (DIMD) as an add-on therapy to second compound.

Throughout this application, various publications are referred to by first author and year of publication. Full citations for these publications are presented in a References section immediately before the claims. Disclosures of the documents and publications cited and those in the References section are hereby incorporated by reference in their entireties into this application in order to more fully describe the state of the art as of the date of the invention described herein.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1: Historic Results from MermaiHD, HART and PRIDE-HD Clinical Trials

Figure 1B:
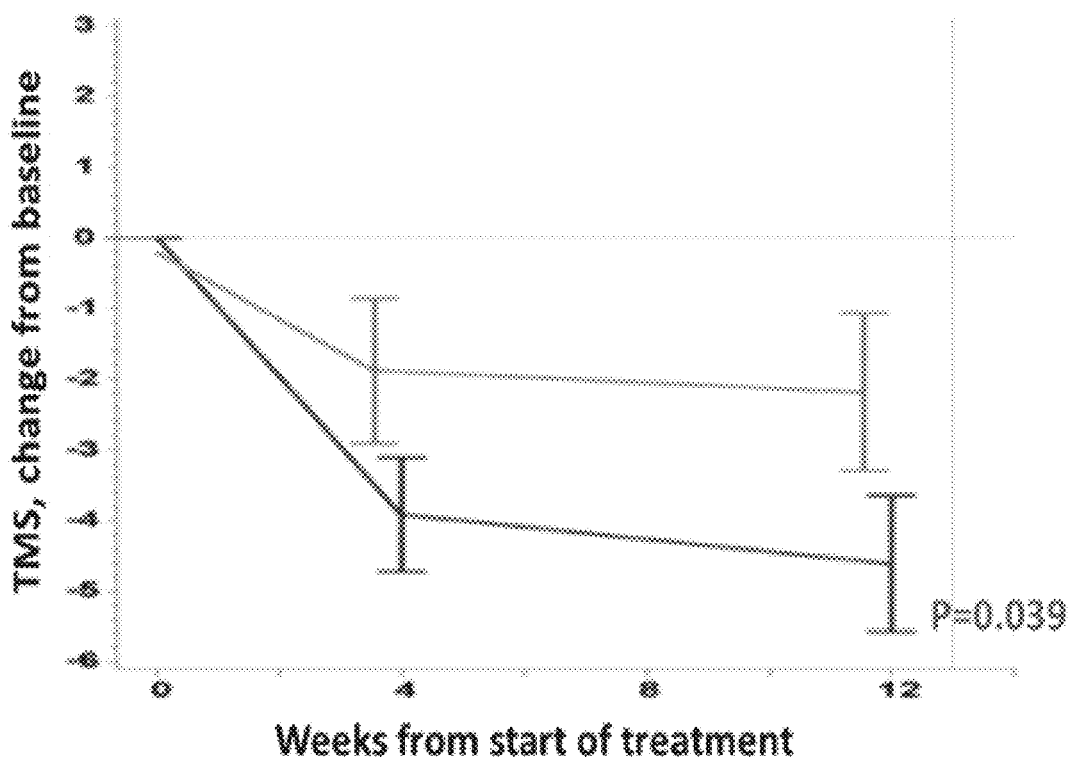

Pridopidine has been evaluated for the treatment of motor symptoms in patients with Huntington's Disease (HD), in three large scale clinical trials. The first two trials, MermaiHD and HART demonstrated that pridopidine, at a dose of 45 mg twice daily (bid) (90 mg/day) significantly improved motor function in HD patients, as measured by the Unified Huntington Disease Rating Scale (UHDRS) Total Motor Score (TMS) (FIGS. 1A and 1B, MermaiHD and HART, respectively. Upper grey line placebo, lower black line 45 mg bid pridopidine) (de Yebenes 2011; Huntington Study Group HART investigators 2013; the entire contents of which are hereby incorporated by reference).

Based on these results, it was hypothesized that high doses of pridopidine would be more efficacious than low doses in alleviating HD motor symptoms. The PRIDE-HD study was conducted as an exploratory, phase 2 dose-ranging, 52-week, double-blind, placebo-controlled study, to evaluate efficacy and safety of pridopidine at doses higher than those used in prior studies, ranging from 45 mg to 112.5 mg bid and further disclosed in PCT Patent Publication No. WO2014/205229 and WO2018/039477. The primary outcome was pridopidine effect on motor function as assessed by the UHDRS-TMS, and exploratory endpoints including Total Functional Capacity (TFC), the most widely accepted tool for assessing disease stage were measured (Shoulson and Fahn 1979; Marder 2000). In the PRIDE-HD study, patients treated with 45 mg bid pridopidine showed a similar improvement in TMS as in HART and MermaiHD. However, none of the high doses of pridopidine (267.5 bid) showed improved efficacy compared to placebo or the 45 mg bid dose.

Figure 2:
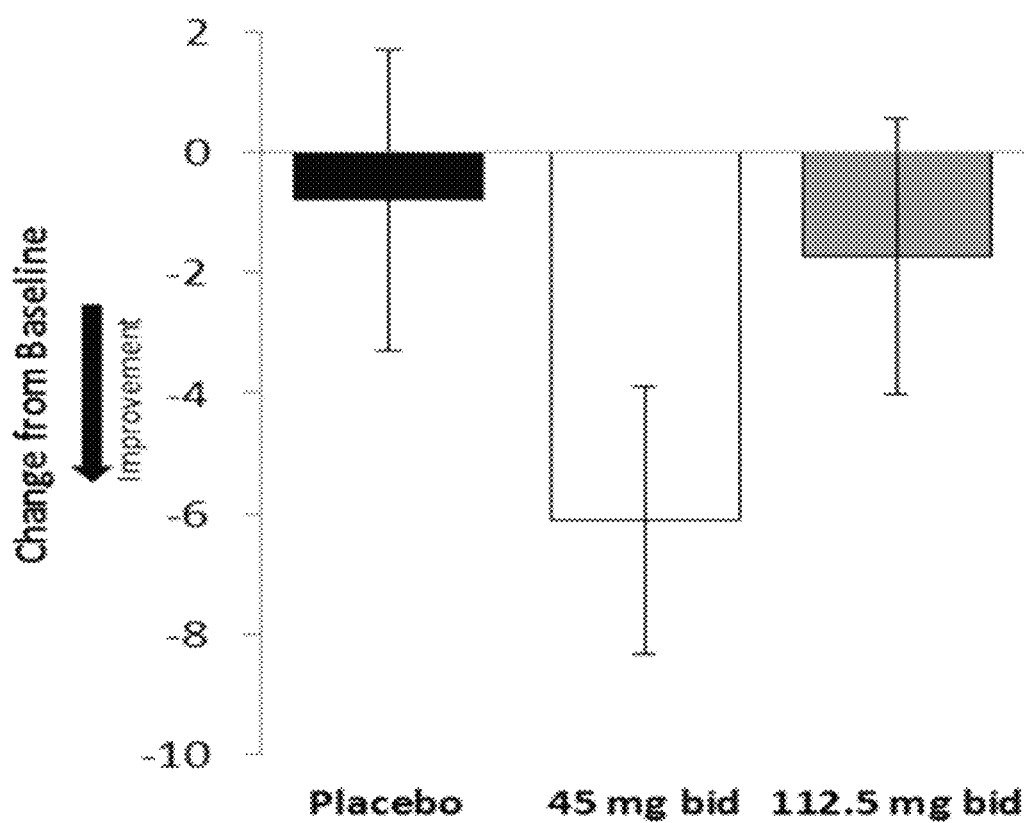

Post hoc analysis, at week 52, in very early stage HD patients (HD stage 1, baseline TFC≥11) revealed there was a trend towards improvement in TMS change from baseline in the 45 mg bid dose treatment compared with placebo at weeks 26 or 52. However, no improvement with the high dose (112.5 mg bid) vs placebo was observed (FIG. 2, 52 weeks). A decrease in TMS (i.e. greater negative value) indicates improvement.

Figure 3:
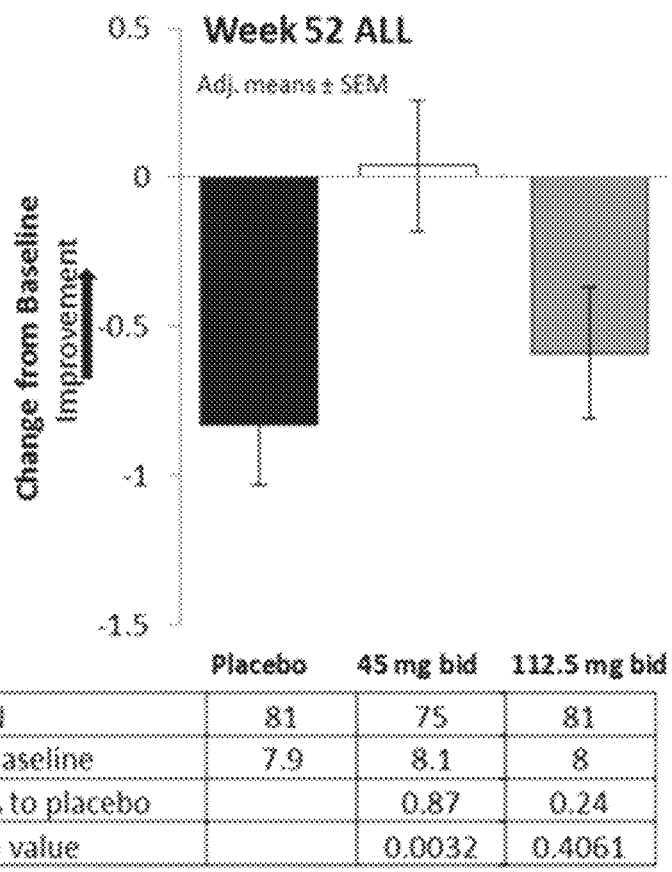

In the TFC pre-specified exploratory endpoint, patients receiving 45 mg bid pridopidine had significantly less decline in the TFC score compared with those receiving placebo at 52 weeks [difference: 0.87 (95% confidence interval: 0.29-1.45), nominal p=0.003] (FIG. 3). Again, the high dose (>90 mg bid) failed to show improvement in TFC decline. An increase in TFC (i.e. higher value) indicates improvement.

It was concluded from the PRIDE-HD study, that the therapeutic effects in HD patients were lost at the high dose, which was similar to placebo.

Example 2: Human Positron Emission Tomography (PET) Study

A phase 1, open label study aimed to evaluate sigma-1 and dopamine-2 receptor (S1R and D2R, respectively) occupancy in the human brain of healthy volunteers (HV) and Huntington's disease (HD) patients two hours after oral administration of immediate release (IR) pridopidine.

The tracer (S)-(−)-[18F]fluspidine (Brust 2014) was used to evaluate S1R target engagement and occupancy and [18F]fallypride (Slifstein 2010) tracer was used to evaluate D2R engagement and occupancy. Pridopidine doses of 0.5, 1, 5, 22.5, 45 and 90 mg were used to evaluate occupancy of the S1R, and 90 mg was used for D2R occupancy.

To minimize variability associated with the potential impact of circadian corticoid plasma level changes, individual scan and re-scan sessions were performed at comparable times of the day for all subjects.

The study consisted of a screening period of up to 8 weeks prior to first dosing of tracer, including a Ti three-dimensional magnetization-prepared rapid acquisition gradient echo (MPRAGE 3D) magnetic resonance imaging (MRI) scan (visit 1), a study period of up to 4 weeks (including visits 2 and 3), and a follow-up visit (visit 4). During the study period, the subjects underwent a baseline PET investigation (PET session 1) at visit 2, and subsequently a post-treatment PET investigation (PET session 2) following a single oral dose of pridopidine at visit 3. Each dose cohort comprised up to 4 subjects. Although every subject of each dose cohort was expected to receive the same dose, it was also possible to change the dose level within a cohort due to the adaptive design of the study.

Results:

The results of the imaging analysis show a S1R occupancy in healthy volunteers of almost 100% with 45 and 90 mg pridopidine, and a S R occupancy of approximately 40% at doses as low as 1 mg pridopidine. This is an unexpectedly high S1R occupancy at even very low doses.

Figure 4:
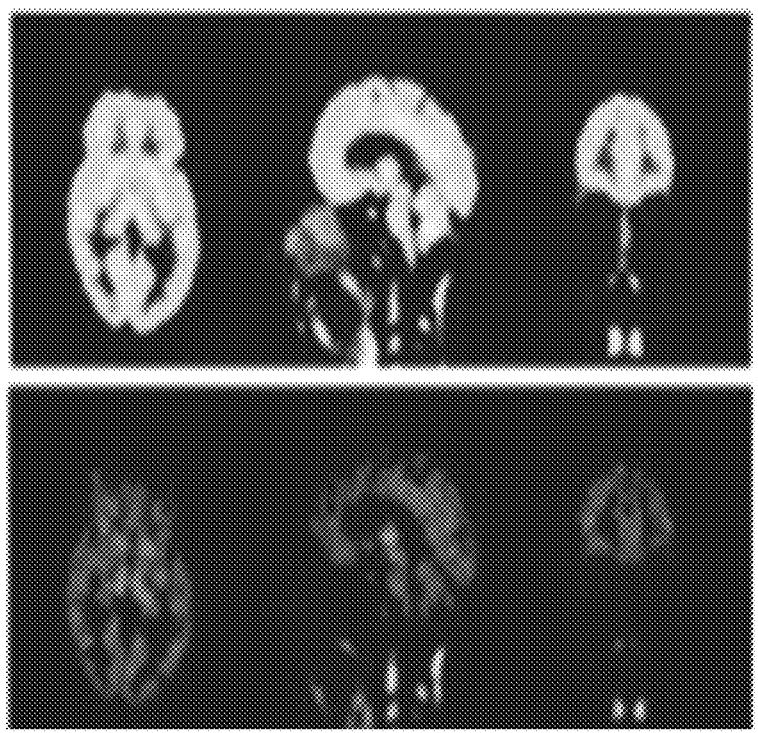
FIG. 4: Reproduction of a PET scan showing levels of S1R occupancy by pridopidine in the brain of healthy volunteers before (upper panel) and after (lower panel) a single dose of 45 mg pridopidine.

Furthermore, at a dose level of 90 mg pridopidine, no differences were observed in drug-induced S1R occupancy between HV and HD patients. FIG. 4 is a PET scan showing levels of S1R occupancy by pridopidine in the brain of healthy volunteers before (bright tissue, upper panel) and after (lower panel) a single dose of 45 mg pridopidine.

There was only minimal D2R blockage (3%) at the 90 mg pridopidine dose, which was only borderline significant, and quantitatively negligible.

The beneficial effects of pridopidine in complex pathologies such as DIMD may be mediated by its interaction with both the S1Rs and the low affinity dopamine receptors (i.e. D2R).

According to the human PET data, pridopidine at 45 mg bid selectively occupies the S1R and not the low affinity targets. In order to modulate the low-affinity CNS receptors implicated in LID, pridopidine doses equivalent to about 100 mg-175 mg bid (200-350 mg/day) were tested in non-human primates (NHP). These doses reached $AUC_{0-24}$ levels above 29,000 h*ng/ml, thereby targeting the low affinity receptors.

Example 3: Non-Human Primate (NHP) Model of Parkinson's Disease

The potential of pridopidine to reduce motor complications of L-DOPA in PD was reported using the 6-OHDA-lesioned rat model (Ponten 2013). Pridopidine, dosed at 25 μmole/kg (corresponding to 8 mg/kg), decreased the L-DOPA-induced sensitization of contraversive-rotation while showing no decrease in the anti-parkinsonian benefit of L-DOPA. A pridopidine dose of 8 mg/kg in the rat, results in $AUC_{0-24}$ levels of ~12000 h*ng/ml which corresponds closely to the $AUC_{0-24}$ levels reached by the 67.5 mg bid dose in humans (12865 h*ng/ml). The human 67.5 mg bid dose is estimated, based on human PET data and PK profile of pridopidine, to exhibit effects similar to the 45 mg bid dose and fully occupy the S1Rs with minimal occupancy of the dopamine receptors (DARs).

The pharmacokinetic (PK) profile and effects of pridopidine (7, 15, 20 and 30 mg/kg, PO) on parkinsonism, dyskinesia (chorea and dystonia) and quality of on-time, in combination with L-DOPA, were assessed in eight female MPTP-lesioned macaques with stable and reproducible LID. The correlation between plasma levels of pridopidine and S1R/D2R receptor occupancies was assessed using both PK data and in-vitro/in-vivo binding data.

The study was conducted in two separate experiments. Study 1 evaluated the effects of pridopidine at 7 and 20 mg/kg in combination with L-DOPA on MPTP-lesioned macaques. In the second study, pridopidine at 15, 20 and 30 mg/kg in combination with L-DOPA was tested. In the first study (study 1) pridopidine was administered 1 hour before L-DOPA. In the second study (study 2) pridopidine was administered 2 hours before L-DOPA.

Material and Methods

Pridopidine hydrochloride (HCl) (4-[3-(Methyl sulfonyl) phenyl]-1-propylpiperidine hydrochloride), MW 317.87 g/mol, highly soluble in water was obtained. For in-vivo PK and behavioral studies, pridopidine was formulated in sterile water with no correction made for the hydrochloride salt. Pridopidine was administered at a dose-volume of 1 ml/kg body weight.

In vitro binding: In vitro binding studies were performed at Eurofins Panlabs Taiwan, Ltd to evaluate IC50/Ki values for affinity of pridopidine to sites including σ1, σ2, adrenergic α2C, α2A, dopamine D3, dopamine D2, serotoninergic 5-HT1A, 5-HT2A, 5-HT7, histamine H3, muscarinic M2, NMDA, 5-HT6 and tachykinin NK1 receptors along with the dopamine transporter (DAT), norepinephrine transporter (NET) and serotonin transporter (SERT). The specific ligand binding to the receptors was defined as the difference between the total binding and the nonspecific binding determined in the presence of an excess of unlabeled ligand. IC50 values were determined by a non-linear, least squares regression analysis using MathIQ™ (ID Business Solutions Ltd., UK). Inhibition constants (Ki) values were calculated using the equation of Cheng and Prusoff 16 using the observed IC50 of the tested compound, the concentration of radio ligand employed in the assay, and the historical values for the KD of the ligand (obtained experimentally at Eurofins Panlabs, Inc.). Hill coefficient (nH), defining the slope of the competitive binding curve, was calculated using MathIQ™. Hill coefficients significantly different than 1.0, may suggest that the binding displacement does not follow the laws of mass action with a single binding site.

Pharmacokinetic Profiling of Pridopidine in the Macaque

Blood sampling: On days of treatment, administration and plasma sampling, macaques were transferred from their home cages and seated in individual primate chairs. Four doses of pridopidine (7, 15, 20 and 30 mg/kg, N=8 per dose), were administered via oral gavage and nine blood samples for drug level analysis collected at 10 minutes prior to drug administration (t=−10 min) and then 10 and 30 min, 1, 2, 4, 6, 8 and 24 h post drug administration. All eight animals received each of the four treatments according to a non-randomized ascending dose design, each separated by a period of one-week. Blood samples (0.5 ml) were placed into K2-EDTA tubes (Becton Dickinson, Mississauga, ON, Canada) and centrifuged at 4° C. for 5 min at 1500 gave and plasma analyzed for pridopidine via LC/MS/MS.

Bioanalysis of pridopidine in macaque plasma: Pridopidine and its internal standard, 4-(3-methylsulfonyl)phenyl)-1-(propyld7)-piperidin-1-ium chloride, were extracted from EDTA plasma by liquid-liquid extraction into acetonitrile as follows: An aliquot of 20 μl of plasma was added to 80 μl of acetonitrile containing 1-10 ng/ml of the internal standard (IS). After centrifuging at 13000 rpm for 8 min, 70 μl of supernatant was isolated and added to 70 μl of sterile water. Finally, an aliquot of 1-10 μl of the mixture was injected into the LC-MS/MS system. For all bioanalytical work 4-(3-methylsulfonyl)phenyl)-1-(propyld7)-piperidin-1-ium chloride was used as the internal standard. In brief, LC-MS/MS analyses were performed on a Shimadzu LC-10AD pump equipped with a CTC-HTS auto-sampler (Zwingen, Switzerland) and a column oven. The MS/MS system was an MDS Sciex API-4000 mass spectrometer with an electrospray ionization probe (Toronto, Canada). Chromatographic separation of the analytes was achieved on an Agilent Zorbax SB-C18 column. The linearity was from 2 ng/ml to 1000 ng/ml with LLOQ of 2 ng/ml. Accuracy values for pridopidine was lower than 15% for all calibration curves and for >75% of each QC sample sets. All PK parameters were calculated per individual animal according to nominal time, that is, within ±5% from schedule time-point by non-compartmental modelling for extravascular administration using WinNonlin 6.3. Below the Limit of Quantification (BLQ) value at time 0 or at a sampling time before the first quantifiable concentration, were treated as zero. BLQ values occurring at the end of the profile were treated as missing. Terminal elimination half-life ($t_{1/2}$) was calculated as ln(2)/λz. The maximum observed plasma concentration ($C_{max}$) and time to reach $C_{mx}$ ($t_{max}$) were obtained directly from the concentration-time data. Area under the plasma concentration-versus-time curve from time 0 to 24 h post dose (AUC$_{0-24}$) was calculated by means of linear trapezoidal linear log interpolation regression analysis.

The pharmacokinetic profile of pridopidine was also characterized in plasma samples collected at multiple timepoints up to 24 h after oral administration. These and other PK data across rodent and primate species were used to assess the relationship between plasma pridopidine levels and central S1R/D2/3R receptor occupancy.

Behavioral Assessment in the MPTP-Lesioned Macaques

Animals: Eight cynomolgus monkeys (*Macaca fascicularis*, 8-14 years of age, 3.0-4.8 kg, Suzhou Xishan-Zhongke Laboratory Animal Company, PRC) were used in this study. Fresh fruit, primate pellets and water were available ad libitum other than at times of overnight fasting (from 5 pm) prior to days of behavioral assessment. The housing rooms were subject to a 12-hour light-dark cycle (lights on 7 a.m.), 20-25° C. in a room containing only animals of the same sex.

MPTP administration and development of motor complications: Animals received once-daily subcutaneous injection of MPTP (0.2 mg/kg in 0.9% sterile-saline, Sigma-Aldrich, Oakville, ON, Canada) for 8-30 days. A parkinsonian syndrome was then allowed to develop over at least a 90-day period, during which time additional MPTP administrations were given as necessary, until animals reached moderate to marked levels of disability. Average cumulative MPTP dose was 33.3 mg. MPTP lesions were allowed to stabilize for a minimum of a further 60-day prior to commencing induction of L-DOPA-induced motor complications. LID, including both choreiform and dystonic dyskinesia, were evoked by chronic L-DOPA treatment (25 mg/kg, Madopar™, Roche, L-DOPA: benserazide, ratio 4:1) for at least 4-months. During this same period animals were acclimatized to the experimental setting, trained to provide blood samples (while restrained in chair) and to receive administration of treatment by oral, intravenous or subcutaneous routes.

L-DOPA dose-finding: Dose-finding observations were conducted to identify a dose of L-DOPA (LDh) intended to produce optimal anti-parkinsonian actions but which was compromised by disabling dyskinesia (range 30-35 mg/kg, mean 32.1 mg/kg). The response to this dose of L-DOPA was assessed to ensure stability and reproducibility within each animal on successive L-DOPA administrations.

Treatments: The assessment of the anti-dyskinetic potential of pridopidine was undertaken in two independent experiments, both of which utilized acute challenge randomized designs. In the first study (study 1), L-DOPA (LDh, PO) was assessed alone or in combination with two doses of pridopidine (7 and 20 mg/kg, PO). In the second study (study 2), L-DOPA (LDh, PO) was assessed alone or in combination with three doses of pridopidine (15, 20 and 30 mg/kg, PO). For both studies, on the day before behavioral observations, food was removed overnight, from 5 p.m. On days of behavioral assessment, treatments were administered to the animals in their home cages. Animals were then transferred to an observation cage for behavioral assessment. Based on the outcome of the PK arms it was decided that vehicle/pridopidine would be given 60 min (study 1) or 120 min (study 2) prior to vehicle/L-DOPA, relative to one another and to start of behavioral observations. The effects of treatments on parkinsonian disability, dyskinesia, duration and quality of anti-parkinsonian benefit (on-time) and activity were assessed and analyzed for a period of 6 hours (h).

Assessment of parkinsonian disability, dyskinesia (chorea and dystonia) and activity: Animals were transferred to individual observation cages (1.5×1.0×1.1 m) and their behavior recorded on HD-video. Rating scales for parkinsonism and dyskinesia adapted from their clinical counterparts (UPDRS pt. III and UDysRS respectively) were used to assess recordings via post-hoc analysis by a movement disorders neurologist blinded to treatment. A measure of total parkinsonian disability as described previously (Johnston 2013) was derived by adding scores for range of movement (score 0-4), bradykinesia (0-3), posture (0-2) and alertness (0-1). Dyskinesia, representative of the maximum of either chorea or dystonia was scored as 0—absent, 1—mild, 2—moderate, 3—marked or 4—severe. Parkinsonian disability and dyskinesia were assessed for 5-min every 10-min, the score given being most representative of each 5-min observation period. Scores were summed for each hour for time-course analyses and across the entire observation period (0-6 h). Thus, for measures parkinsonian disability and dyskinesia, the maximum scores possible (equating to severe) over the 0-6 h period were 360 and 144 respectively.

The duration of anti-parkinsonian action, on-time, was defined as the number of minutes for which the bradykinesia score was zero. In addition, the duration of on-time associated with dyskinesia of varying severity was calculated as follows. On-time with disabling dyskinesia, 'bad'-on-time was calculated the number of minutes for which the bradykinesia score was zero while the dyskinesia score was greater than 2. Meanwhile, on-time without disabling dyskinesia, 'good'-on-time represents the number of minutes for which the bradykinesia score is zero while the dyskinesia score is 2 or less.

Statistical analyses: Data derived from assessment of duration and quality of on-time were plotted as mean±s.e.m. Statistical analyses for these data were performed using parametric repeated measures one- or two-way ANOVA as appropriate, followed by Holm-Sidak multiple comparison's tests. Data for measures of parkinsonian disability and dyskinesia were graphed, where appropriate, as median scores alone (time course) or box and whisker plots (cumulated totals). Time course data for parkinsonian disability and dyskinesia were first ranked within each animal across all treatments using Excel's RANKAVG function. These transformed data were then analyzed in GraphPad Prism (v 7.02) and subjected to non-repeated measures 2-way ANOVA followed by Holm-Sidak multiple comparison tests. Cumulated disability and dyskinesia data were analyzed using a Friedman test followed by a Dunn's Multiple Comparisons test.

Results

In vitro pridopidine receptor binding profile.

Pridopidine binding was evaluated in radioligand binding assays as described in the materials and methods. In-vitro binding assays were performed against novel receptors and as validation of previously reported targets for pridopidine. Pridopidine was found to have highest affinity for the S1R with an IC50 of 0.14 μM (140 nM). Pridopidine also shows low-affinity binding to additional receptors, in the micromolar range including serotonin (or 5-hydroxytryptamine [5-HT]) 5-HT1A, 5-HT2A, and 5-HT7; adrenergic alpha-1, adrenergic alpha-2A and alpha-2C; dopamine D3; muscarinic M2; and histamine H3 (see Table 1, below). Only negligible or no binding of pridopidine against the dopamine D2 receptors (D2R) was detected. Additional targets were tested including NMDAR, 5-HT6, Tachykinin NK1, Dopamine transporter (DAT), Norepinephrine transporter (NET) and the Serotonin transporter (SERT) with no observed binding.

TABLE 1

| Target receptor | IC$_{50}$ (μM) | K$_i$ (μM) | nH |
|---|---|---|---|
| Sigma-1 (σ$_1$R) | 0.14 | 0.057 | 0.87 |
| Adrenergic α$_{2C}$ | 3.56 | 1.58 | 0.76 |
| Dopamine D$_3$ | 4.79 | 1.63 | 0.90 |
| Serotonin 5-HT$_{1A}$ | 6.36 | 3.63 | 0.72 |
| Sigma-2 (σ$_2$R) | 7.16 | 5.45 | 0.80 |
| Serotonin 5-HT$_{2A}$ | 24.5 | 7.00 | 0.81 |
| Serotonin 5-HT$_7$ | 14.8 | 8.51 | 1.02 |
| Adrenergic α$_{2A}$ | 22.0 | 11.0 | 0.98 |
| Histamine H$_3$ | 37.6 | 18.3 | 0.85 |
| Muscarinic M$_2$ | 58.1 | 24.4 | 0.62 |
| Dopamine D$_2$ | 88.4 | 29.5 | 0.94 |

IC$_{50}$ = half maximum inhibitory concentration K$_i$ = inhibition constant calculated using the equation of Cheng and Prusoff. nH = Hill coefficient, defining the slope of the competitive binding curve, was calculated using MathIQTM.

Pharmacokinetic Profile of Pridopidine in the MPTP-Lesioned Macaque

All doses of pridopidine assessed (7, 15, 20 and 30 mg/kg) were well tolerated. Oral administration of pridopidine 7, 15, 20 and 30 mg/kg, was associated with geometric mean C max values of 384, 952, 1487 and 2676 ng/ml (corresponding to 1.4, 3.4, 5.3 and 9.5 μM, respectively) and AUC$_{0-24}$ values of 1214, 4905, 8207 and 22987 ng*h/ml (corresponding to 4.3, 17.5, 29.2 and 81.8 h*μM)

S1R and moderate affinity receptor occupancies were assessed as indicated in Table 2, below, using (i) known binding affinities of pridopidine to human and rodent receptors in vitro (ii) published in vivo PET imaging in rats (Sahlholm 2015) and non-human primate (NHP), and (iii) the extensive pharmacokinetic profiling of pridopidine in the different species.

TABLE 2

Expected Occupancy of Rodent and NHP S1R and D2R at Pridopidine Doses

| Species | Dose (PO) | C$_{max}$ (ng/ml) | C$_{max}$ (μM) | AUC$_{0-24}$ (h*ng/ml) | AUC$_{0-24}$ (h*μM) | % σ$_1$R occupancy | % D$_2$R occupancy |
|---|---|---|---|---|---|---|---|
| Rat | 3 mg/kg | 281 | 1 | 2276 | 8 | 60 | 0 |
| | 15 mg/kg | 1407 | 5 | 11380 | 41 | 85 | 0 |
| | 60 mg/kg | 5628 | 20 | 45519 | 162 | >85 | 45 |
| NHP | 7 mg/kg | 384 | 1.4 | 1214 | 4.3 | 60-80 | <15 |
| | 15 mg/kg | 952 | 3.4 | 4905 | 17.5 | >80 | 15 |
| | 20 mg/kg | 1487 | 5.3 | 8207 | 29.2 | >80 | 25 |
| | 30 mg/kg | 2676 | 9.5 | 22987 | 81.8 | >80 | 40 |

The non-human primate (NHP) data is most relevant to the following discussion. C max values for rat and NHP as a function of oral pridopidine dose are based on internally accumulated PK data (supplementary) in addition to data presented here. Rat σ1R and D2R occupancy data are based on in vivo measurements at 3 and 15 mg/kg (Sahlholm 2015), NHP D2R occupancy data is based on in vivo PET imaging with the specific D2R ligand 11C-raclopride. NHP σ1R occupancy data are extrapolated from in vitro binding investigations with 3H-fluspidine, known and specific σ1R tracer, against human σ1R.

It is speculated that at the low doses (7, 15 mg/kg, study 1), pridopidine's effect is mainly mediated by the S1R, while at the higher dose (30 mg/kg and 20 mg/kg (study 2), pridopidine binds the S1R as well as a more complex activity of pridopidine is initiated by binding to the additional low affinity receptors.

Orally administered pridopidine was well tolerated at all doses assessed. The effects of acute combination of pridopidine with LDh on parkinsonian disability, dyskinesia (including dystonic and choreiform), and duration and quality of on-time are shown in FIGS. 5A,5B-10.

Figure 5A:
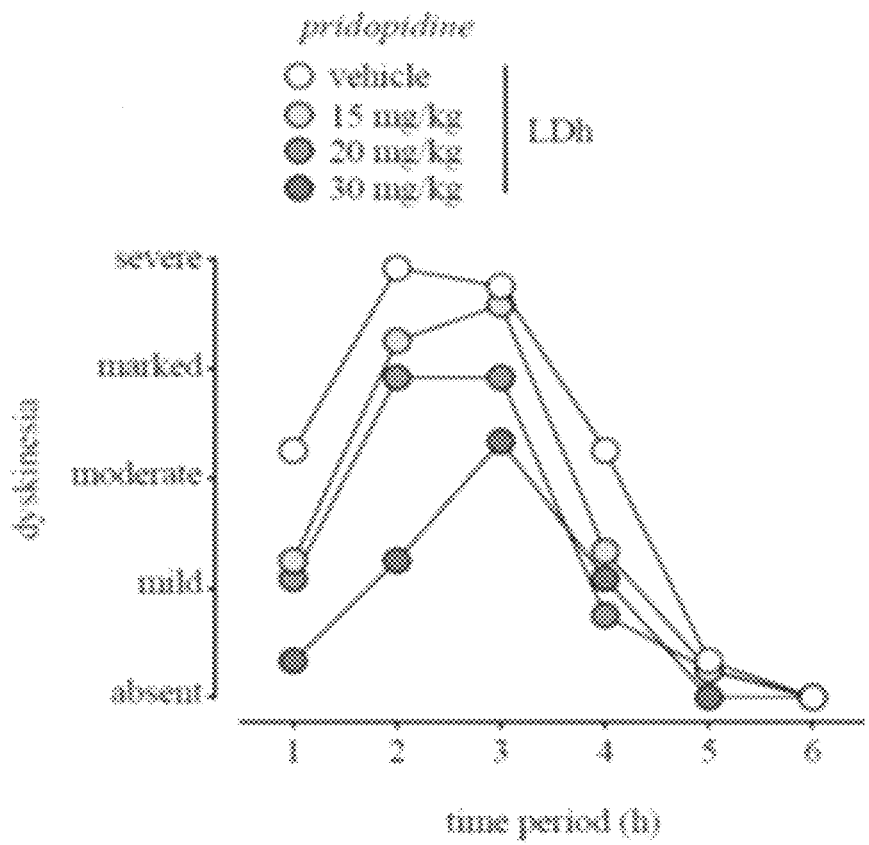

Table 3 shows the 6 hour data presented in FIG. 5A for Dyskinesia (time course) in study 2. Pridopidine reduces established dyskinesia evoked by high L-DOPA.

TABLE 3

| | LDh-vehicle (hr) | | | | | |
|---|---|---|---|---|---|---|
| pridopidine | 1 | 2 | 3 | 4 | 5 | 6 |
| 15 mg/kg | ns | ns | ns | ns | ns | ns |
| 20 mg/kg | * | ns | ns | ns | ns | ns |
| 30 mg/kg |  | * | ns | ns | ns | ns | ns: not significant.
*//* represents P < 0.05, P < 0.01 or P < 0.001 cf. vehicle-treatment. 2-way RM ANOVA with Holm-Sidak's test or Friedman test with DUNN'S test Pridopidine Reduced Established L-DOPA-Induced Dyskinesia in the MPTP-Lesioned Macaque Pridopidine produced a significant and dose-dependent reduction in dyskinesia evoked by LDh. Examining the whole 6 hr time-course revealed a significant effect of combination treatment (F (3, 28)=4.981, P=0.0068) but not time (F (5, 140)=0, P>0.9999) or the interaction of treatment and time (F (15, 140)=0.9595, P=0.5011) on levels of dyskinesia (2-way, RM-ANOVA). Compared to LDh-vehicle treatment, there was a significant decrease in dyskinesia during the first hour (20 mg/kg) and first and second hours (30 mg/kg) after start of observation in response to LDh when combined with pridopidine, with median levels remaining between moderate and marked (20 mg/kg) or mild to moderate (30 mg/kg) (all P<0.05) (Table 3). Assessing levels of dyskinesia cumulated over the two-hour period after start of observations (0-2 h period) revealed a significant effect of pridopidine combination treatment (0-2 h; Friedman Statistic (FS)=11.66, P=0.0087, FIG. 5B) on levels of dyskinesia evoked by LDh. Median levels of dyskinesia in LDh-treated animals combined with high-dose pridopidine (30 mg/kg) were reduced by 71% compared to those seen following LDh-vehicle such that median levels were below mild (non-disabling) (P<0.01).

Figure 6A:
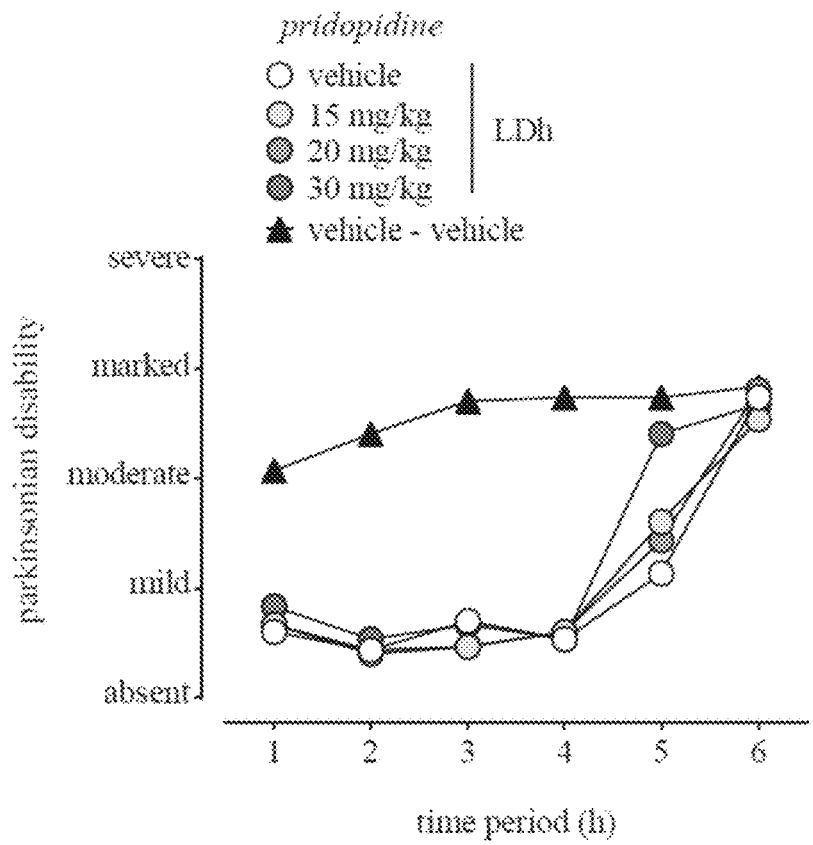
FIG. 6A: Graph showing Parkinsonian disability (time course 0-6 hr): Pridopidine does not reduce the anti-parkinsonian benefit of L-DOPA (study 2). Y axis is severity of parkinsonian disability, X axis shows time course in hours. Triangles: vehicle/vehicle (no L-DOPA and no pridopidine) treated animals, circles: L-DOPA/vehicle or L-DOPA/pridopidine treated animals.
Figure 6B:
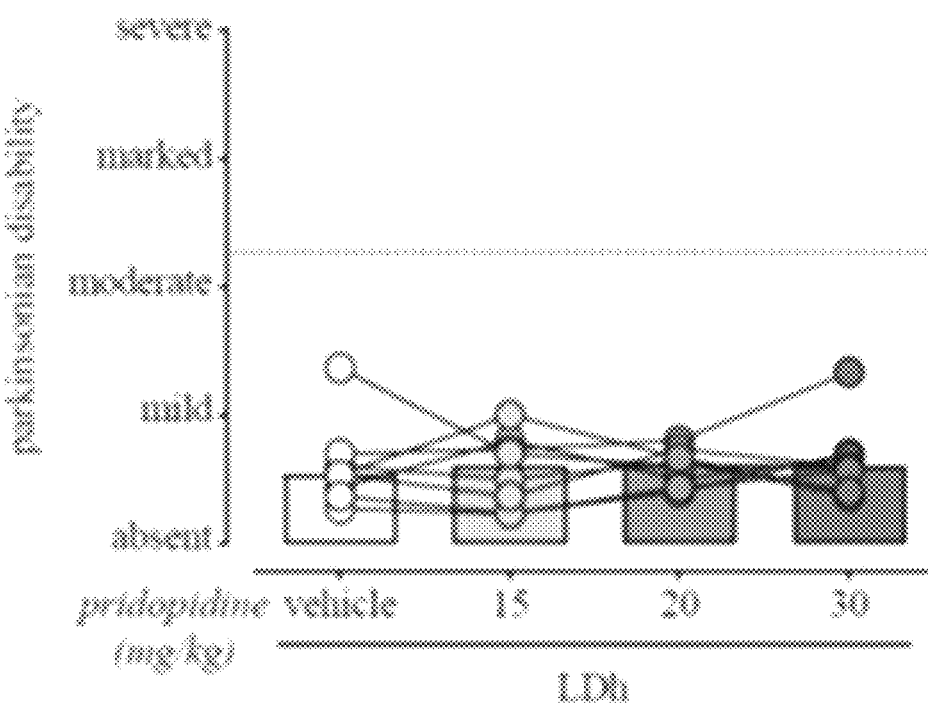
FIG. 6B: Bar graph showing Parkinsonian disability (0-2 hr accumulated) Pridopidine does not reduce the anti-parkinsonian benefit of L-DOPA (study 2). Y axis is severity of parkinsonian disability, X axis shows pridopidine doses.

FIG. 6A time course (0-6 hr) and FIG. 6B bar graph (0-2 hour accumulated) show levels of Parkinsonian disability. Pridopidine did not reduce the anti-parkinsonian benefit of L-DOPA (study 2).

Table 4 shows that there were no significant changes in parkinsonism in L-DOPA treated animals, resulting from additional therapy with pridopidine at all doses, as shown in FIG. 6A (study 2).

TABLE 4

Pridopidine had no adverse effect on the
anti-parkinsonian benefit of L-DOPA

| pridopidine | LDh-vehicle (hr) | | | | | |
|---|---|---|---|---|---|---|
| | 1 | 2 | 3 | 4 | 5 | 6 |
| 15 mg/kg | ns | ns | ns | ns | ns | ns |
| 20 mg/kg | ns | ns | ns | ns | ns | ns |
| 30 mg/kg | ns | ns | ns | ns | ns | ns | ns: not significant

Figure 5B:
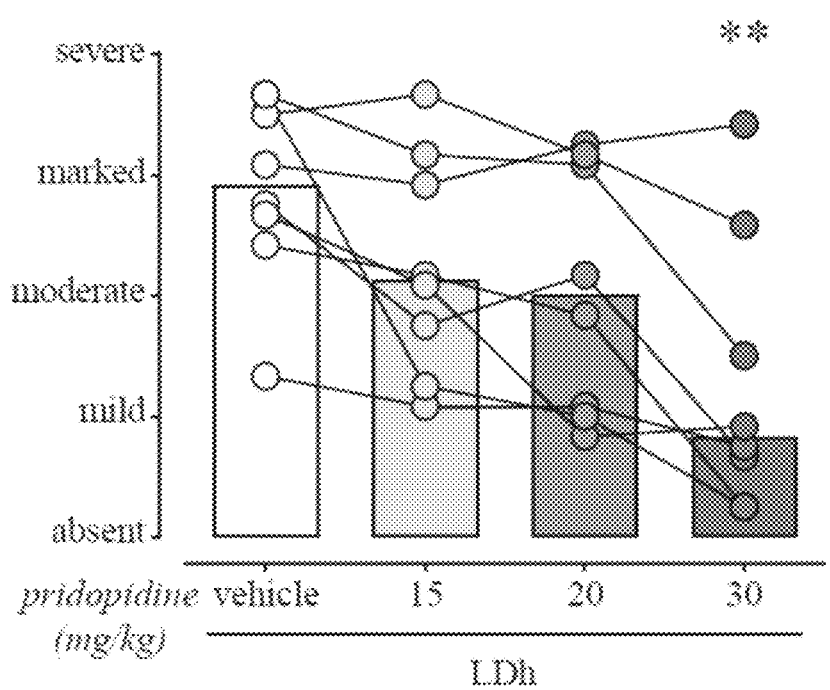

Levels of dyskinesia (FIG. 5A-5B) and parkinsonism disability (FIG. 6A-6B) were assessed over 6 hour period (FIGS. 5A and 6A) or cumulated across the 0-2 hour period of peak-effect (FIGS. 5B and 6B). Data are median (Tables 3 and 4) with individual values (FIGS. 5A-5B and 6A-6B). N=8 for all treatment groups. *//* represents P<0.05, P<0.01 or P<0.001 of vehicle-treatment. 2-way RM ANOVA (Tables 3 and 4) with Holm-Sidak's test or Friedman test with DUNN'S test (FIGS. 5A-5B and 6A-6B).

Figure 7A:
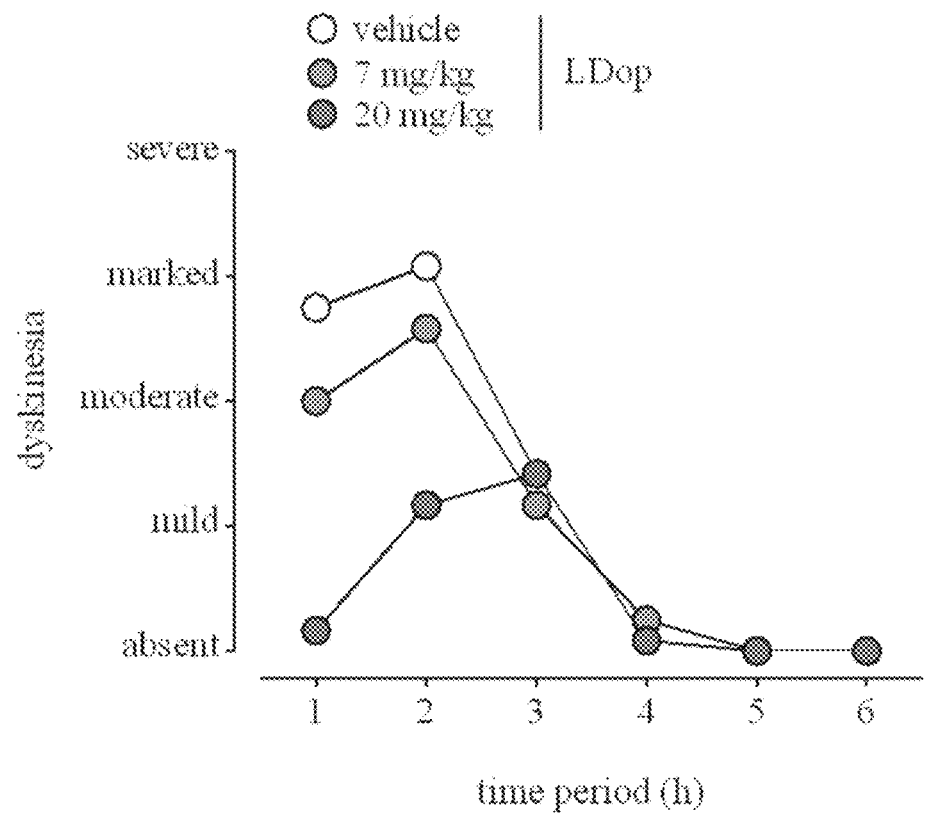
FIG. 7A: Graph showing dyskinesia (time course 0-6 hr) (study 1): Pridopidine reduces established dyskinesia evoked by high dose L-DOPA. Y axis is severity of dyskinesia, X axis shows time course in hours.
Figure 7B:
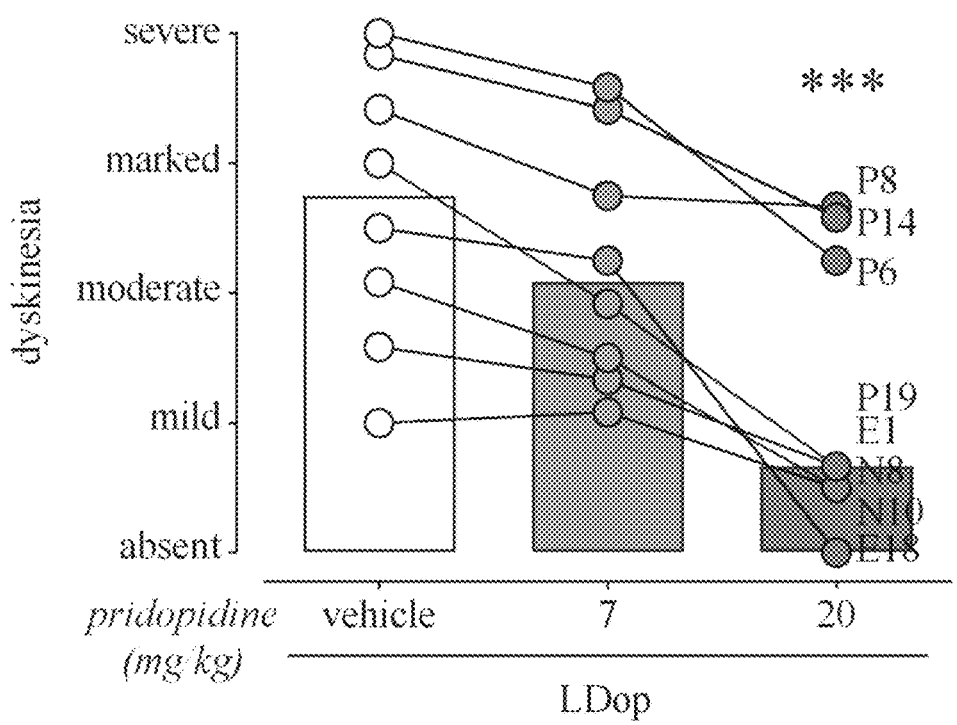
FIG. 7B: Bar graph showing dyskinesia (0-2 hr accumulated) (study 1): Pridopidine reduces established dyskinesia evoked by high dose L-DOPA. Y axis is severity of dyskinesia, X axis shows pridopidine doses.

Data from study 1: Pridopidine produced a significant and dose dependent reduction in dyskinesia evoked by L-DOPA in study 1 (FIG. 7A-7B). FIG. 7A examining the whole 6 hr time course and FIG. 7B bar graph showing individual animals at 0-2 hours accumulated after L-DOPA administration. This decrease was observed in the absence of any change to the total duration of on-time or extent of anti-parkinsonian benefit of L-DOPA. The lower-dose of pridopidine (7 mg/kg) did produce a modest decrease in the anti-parkinsonian benefit afforded by L-DOPA during the first two hours of observation (from study 1, data not shown).

Figure 8A:
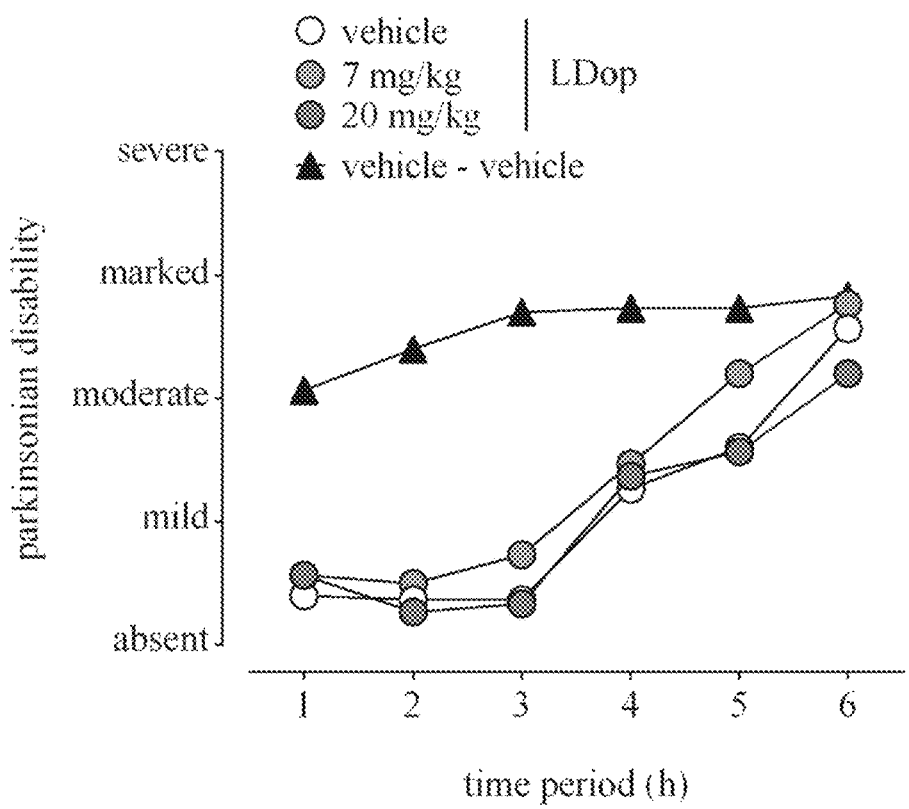
FIG. 8A: Graph showing Parkinsonian disability (time course 0-6 hr): Pridopidine does not reduce the anti-parkinsonian benefit of L-DOPA (study 1). Y axis is severity of parkinsonism (parkinsonian disability), X axis shows time course in hours.
Figure 8B:
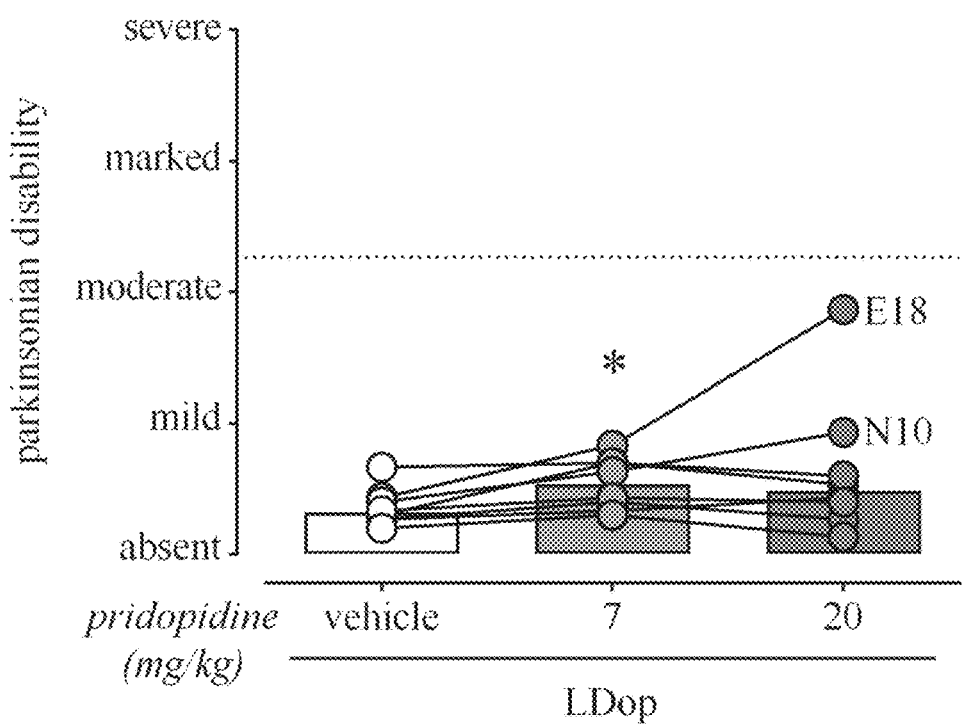
FIG. 8B: Bar graph showing Parkinsonian disability (0-2 hr accumulated): Pridopidine does not reduce the anti-parkinsonian benefit of L-DOPA (study 1). Y axis is severity parkinsonian disability, X axis shows pridopidine doses.

Pridopidine did not reduce the beneficial anti-parkinsonism effect of L-DOPA (FIG. 8A-8B). FIG. 8A examining the whole 6 hr time course and FIG. 8B is a bar graph showing individual animals at 0-2 hours after L-DOPA.

Data are medians (FIGS. 7A, 8A) with individual values (FIGS. 7B, 8B). N=8 for all treatment groups. *//* represents P<0.05, P<0.01 or P<0.001 cf. vehicle-treatment, 2-way ANOVA with Holm-Sidak PHT (FIGS. 7A, and 8A), Friedman's test with Dunn's PHT (FIGS. 7B, 8B,). For reference (but not included in statistical analyses, ▲ describes data in response to vehicle-vehicle treatment).

Effects of Pridopidine on L-DOPA-Induced Dystonia and Chorea

Pridopidine produced a significant and dose-dependent reduction in levels of L-DOPA-induced dystonia evoked by LDh. Examining the whole 6 hr time-course revealed a significant effect of combination treatment (F (3, 28)=7.017, P=−0.0012) but not time (F (5, 140)=0, P>0.9999) or the interaction of treatment and time (F (15, 140)=0.9735, P=0.4863) on levels of dystonia (2-way, RM-ANOVA, FIG. 9A, Table 5).

TABLE 5

Effect of escalating doses of pridopidine
on L-DOPA induced Dystonia

| pridopidine | LDh-vehicle (hr) | | | | | |
|---|---|---|---|---|---|---|
| | 1 | 2 | 3 | 4 | 5 | 6 |
| 15 mg/kg | ns | ns | ns | ns | ns | ns |
| 20 mg/kg | * | ns | ns | ns | ns | ns |
| 30 mg/kg |  | * | * | ns | ns | ns | ns: not significant.
*//* represents P < 0.05, P < 0.01 or P < 0.001 cf. vehicle-treatment. 2-way RM ANOVA with Holm-Sidak's test or Friedman test with DUNN'S test Comparing to LDh-vehicle treatment revealed a significant decrease in dystonia during the first hour (20 and 30 mg/kg) and second and third hours (30 mg/kg) after start of observation in response to LDh when combined with pridopidine, with median levels remaining between moderate and marked (20 mg/kg) or mild to moderate (30 mg/kg) (all P<0.05). Assessing levels of dystonia cumulated over the 0-2 h period revealed a significant effect of pridopidine combination treatment (0-2 h; Friedman Statistic (FS)=11.88, P=0.0078, FIG. 9B) on levels of dystonia evoked by LDh administration. Median levels of dystonia in animals treated with LDh combined with high-dose pridopidine (30 mg/kg) were reduced (by 72%) compared to that seen following LDh-vehicle such that median levels of dyskinesia were below mild (non-disabling) (P<0.01).

Figure 9A:
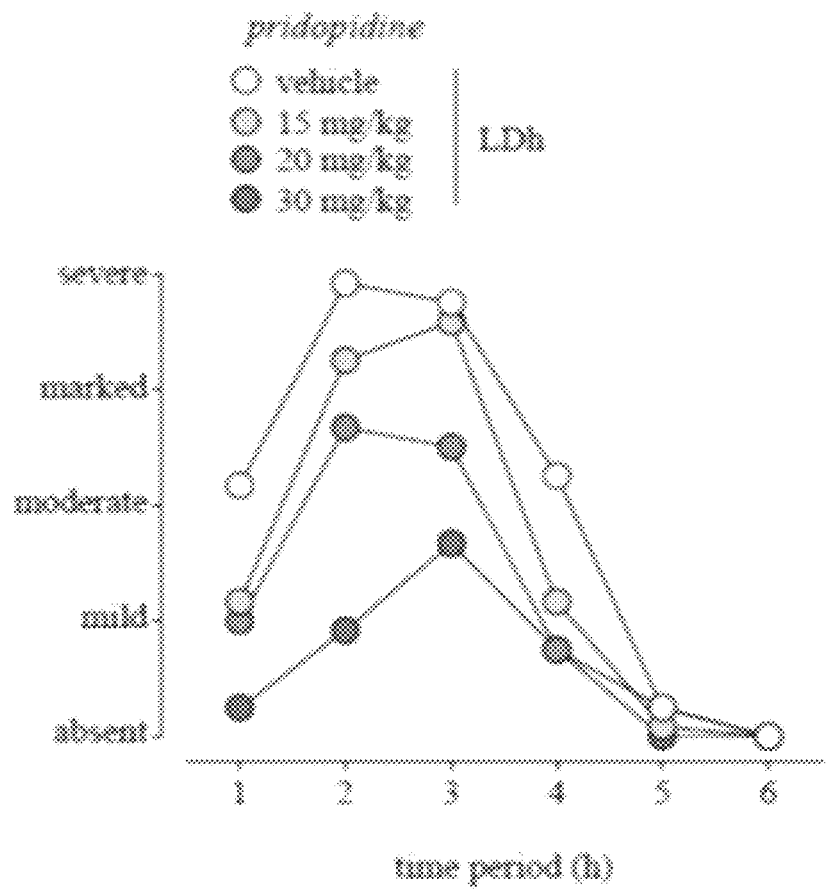
FIG. 9A: Graph showing that pridopidine reduces L-DOPA induced dystonia (study 2). Y axis is severity of dystonia, X axis time course 0-6 hours.
Figure 9B:
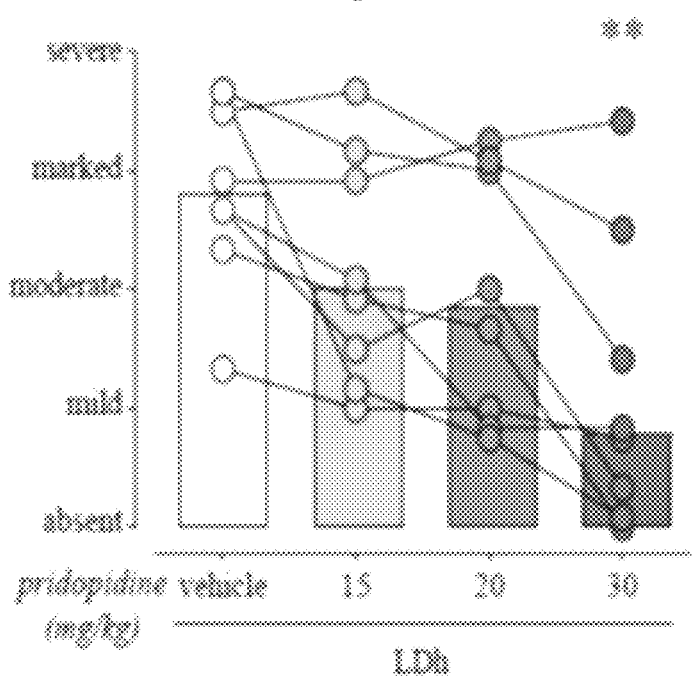
FIG. 9B: Bar graph showing pridopidine effect on L-DOPA induced dystonia (0-2 hr accumulated) (study 2): Pridopidine reduces established dystonia evoked by high dose L-DOPA. Y axis is severity of dystonia, X axis shows pridopidine doses.
Figure 9C:
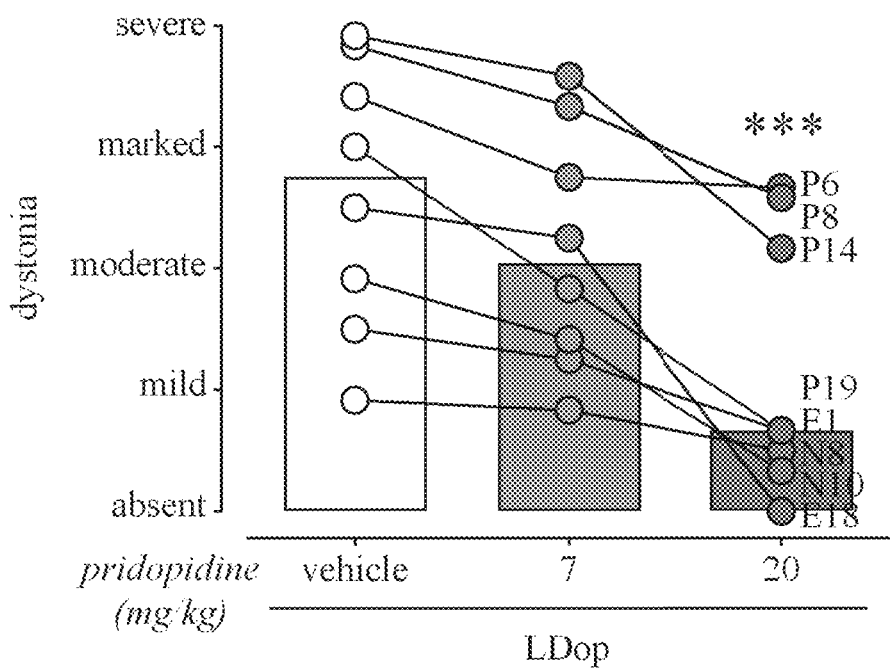
FIG. 9C: Bar graph showing pridopidine effect on L-DOPA induced dystonia (0-2 hr accumulated) (study 1): Pridopidine reduces established dystonia evoked by high dose L-DOPA. Y axis is severity of dystonia, X axis shows pridopidine doses.

Pridopidine significantly reduced L-DOPA induced dystonia (study 1), in a dose dependent manner. FIG. 9C, shows cumulated dystonia levels at 0-2 hours post L-DOPA administration and a significant and dose-dependent reduction of L-DOPA-induced dystonia levels over a 0-2 hr time period with pridopidine.

Figure 9D:
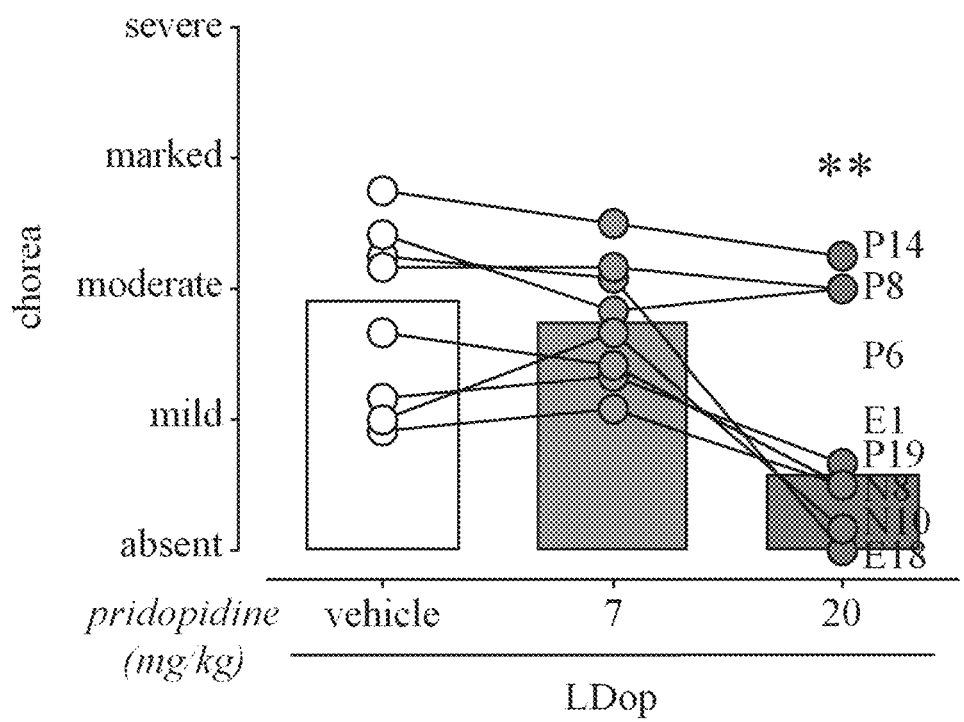
FIG. 9D: Bar graph showing pridopidine effect on L-DOPA induced chorea (0-2 hr accumulated) (study 1): Pridopidine reduces chorea evoked by high dose L-DOPA. Y axis is severity of chorea, X axis shows pridopidine doses.

Pridopidine significantly reduced L-DOPA induced chorea. FIG. 9D) (study 1) shows cumulated chorea levels at 0-2 hours post L-DOPA administration and a significant and dose-dependent reduction of L-DOPA-induced chorea levels over a 0-2 hr time period with pridopidine.

In study 2 animals exhibited low baseline levels of chorea which made it was not appropriately powered to assess effect on chorea.

Effects of Pridopidine on Duration and Quality of On-Time

Figure 10:
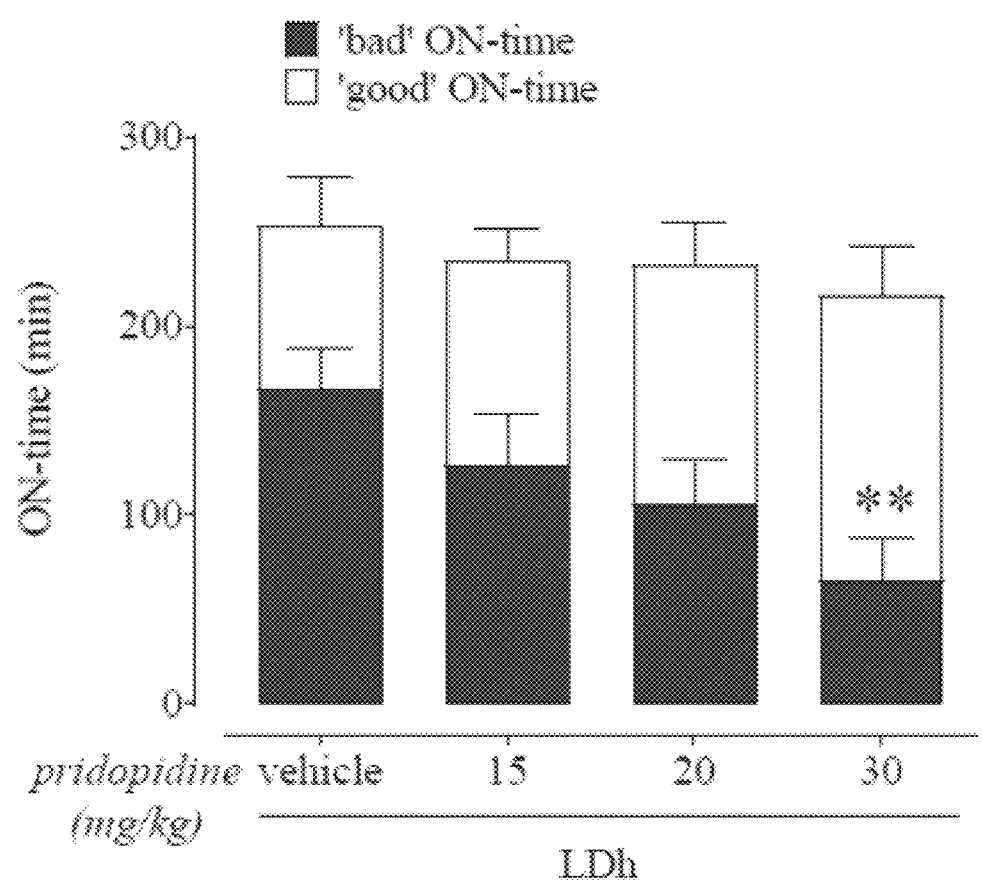

Pridopidine produced no change in the total duration of on-time but improved the quality of on-time associated with LDh (FIG. 10; "bad" on time black, "good" on time white, y axis=minutes). Thus, pridopidine did not negatively impact on the duration of anti-parkinsonian benefit of L-DOPA but rather altered the associated quality thereof in terms of the proportion that was either 'good' or 'bad' (on-time associated with non-disabling or disabling dyskinesia respectively). Specifically, assessed over the six-hour period of observation while there was no effect of treatment (F (3, 21)=1.659, P=0.2062), there was significant effect of on-time subtype (total, good or bad; F (2, 14)=18.29, P=0.0001) and the interaction of treatment and subtype (F (6, 42)=2.887, P=0.0190) on duration and quality of on-time (2-way, RM-ANOVA, FIG. 10). Post-hoc Holm-Sidak's analysis revealed no difference in either duration of total on-time or proportion of on-time that was of 'good' quality in response to LDh when combined with any dose of pridopidine compared to that observed following LDh-vehicle treatment. By contrast, pridopidine produced a significant reduction in 'bad' quality on-time with a decrease of 60% evident following administration of the 30 mg/kg dose compared to vehicle treatment (66 min cf. 168 min respectively, P<0.01).

Discussion

The cynomolgus macaques employed in this study were rendered parkinsonian with MPTP. The extent of lesion produced by this regimen (Johnston 2013) is comparable to that observed in advanced Parkinson's patients and typical of MPTP-lesioned animals with robust parkinsonism. The doses of L-DOPA employed as part of the current study provided maximal anti-parkinsonian benefit, typically with a duration of ~3 h but this was compromised by disabling dyskinesia induced by L-DOPA (greater than moderate levels). Indeed, the duration of L-DOPA efficacy was mirrored by the duration of L-DOPA-induced dyskinesia. Although those doses of L-DOPA administered in clinical settings are generally lower, on a mg/kg basis than those administered to the MPTP-lesioned macaque even corrected for human equivalent dosing (HED), we have shown that they deliver equivalent plasma pharmacokinetic profiles to those achieved with clinically relevant L-DOPA doses as given to PD patients (Dizdar 1999; Huot 2012).

The cellular target of pridopidine was evaluated in various in vitro binding assays. Pridopidine binds with highest affinity to the Sigma-1 receptor (S1R, binding IC50~100 nM), approximately 100 fold higher affinity compared to an earlier described target, the Dopamine D2R (IC50~10 µM) and to several other central nervous system (CNS) receptor targets, including, serotonin (5-hydroxytryptamine [5-HT]) 5-HT1A, 5-HT2A, and 5-HT7; adrenergic alpha-1, adrenergic alpha-2A and alpha-2C; dopamine D3; and muscarinic M2, all in the mid micromolar range.

All doses of pridopidine assessed (7, 15, 20 and 30 mg/kg) were well tolerated. Oral administration of pridopidine 7, 15, 20 and 30 mg/kg, was associated with geometric mean $C_{max}$ values of 384, 952, 1487 and 2676 ng/ml (corresponding to 1.4, 3.4, 5.3 and 9.5 µM, respectively) and $AUC_{0-24}$ values of 1214, 4905, 8207 and 22987 ng*h/ml (corresponding to 4.3, 17.5, 29.2 and 81.8 h*µM) Receptor occupancy was estimated using (i) known binding affinities of pridopidine to human and rodent S1R and D2R in vitro (ii) in vivo PET imaging in rats, NHP and human, and (iii) pharmacokinetic PK profiling in the different species. Plasma exposures observed following the low, ineffective doses (7 mg/kg and 15 mg/kg (study 1), and 20 mg/kg which exhibited a trend for an effect but not significant in study 2), is expected to be associated with full S1R occupancy>80% but with negligible engagement of low affinity dopamine receptors, with, occupancy about 10%. Plasma exposures following the high, effective dose (30 mg/kg (or 20 mg/kg in study 1)) is expected to saturate the S1R (>80% occupancy) and have a higher (about 40%) occupancy of the low affinity dopamine receptors.

In MPTP-lesioned NHPs, high-dose pridopidine produced a significant and meaningful decrease in LID without compromising the anti-parkinsonian benefit of L-DOPA. A complex pharmacology may underlie the effectiveness of pridopidine against LID.

Contrary to what was observed in HD, administration of pridopidine at low doses was ineffective against LID whereas high doses of pridopidine exhibited beneficial effects in reducing in LID in a PD NHP model. In HD, by contrast, pridopidine is beneficial at low doses but no benefit is observed at high doses. These studies provide data to support the use of high-dose pridopidine for the treatment of dyskinesia and DIMD, including LID in PD patients.

Example 4: Therapy for Treating LID in PD Patients

Periodically orally administering of pridopidine (greater than 100 mg/day, for example 105 mg/day, 110 mg/day, 135 mg/day, 150 mg/day, 175 mg/day, 180 mg/day, 200 mg/day, 225 mg/day, 250 mg/day, 300 mg/day, 350 mg/day, 400 mg/day) as an add-on therapy for a human subject afflicted with LID who is already receiving levodopa provides a clinically meaningful advantage in reducing the symptoms of LID.

The therapy provides efficacy in treating the patient without undue adverse side effects or affecting the safety of the treatment:

1. The therapy is effective in improving symptoms of dyskinesia.

2. The therapy does not produce any significant side effects such as sedation and depression.

3. The therapy does not affect the anti-parkinsonian benefit of L-DOPA.

4. The therapy improves the bad quality on-time evoked by levodopa.

Example 5: Add-on Therapy for Treating LID in PD Patients

Periodically orally administering of pridopidine (45 mg/day, 90 mg/day, 135 mg/day or 180 mg/day) as an add-on therapy for a human subject afflicted with LID who is already receiving amantadine provides a clinically meaningful advantage and is more effective (provides at least an additive effect or more than an additive effect) in treating the patient than when administering pridopidine alone (at the same dose).

The add-on therapies also provide efficacy (provides at least an additive effect or more than an additive effect) in treating the patient without undue adverse side effects or affecting the safety of the treatment:

The add-on therapy is effective (provides at least an additive effect or more than an additive effect) in improving symptoms of dyskinesia.

The add-on therapy does not produce any significant side effects such as sedation and depression.

Example 6: Treating DIMD

Periodically orally administering of pridopidine (45 mg/day, 90 mg/day, 135 mg/day or 180 mg/day) as an add-on therapy for a human subject afflicted with a DIMD who is already receiving or has received at least one of antidepressant, an antipsychotic, an antiepileptic, an antimicrobial, an antiarrhythmic, a mood stabilizer, a gastrointestinal drug provides a clinically meaningful advantage in treating the patient.

The therapy also provides efficacy in treating the patient without undue adverse side effects or affecting the safety of the treatment:

The therapy is effective (provides at least an additive effect or more than an additive effect) in improving some or all of the symptoms of DIMD.

The therapy does not produce any significant side effects such as sedation and depression.

Example 7: Estimated Occupancy of Human $\sigma_1 R$ and $D_2 R$ Receptors

In vivo $\sigma_1 R$ and $D_2 R$ occupancies were calculated using (i) known binding-affinities of pridopidine to human in-vitro; (ii) in vivo positron-emission tomography imaging in humans and (iii) the extensive PK profiling of pridopidine in the different species.

TABLE 6

Estimated Occupancy of the Human σ1R and D2R Receptors at Various Pridopidine Doses

| Species | Dose | Cmax (ng/ml) | AUC0-24 (h*ng/ml) | % σ1R occupancy | % D2R occupancy |
|---|---|---|---|---|---|
| Human | 45 mg BID, (90 mg/day, PO) | 618 | 8600 | >90 | ~3 |
|  | 90 mg BID, (180 mg/day, PO) | 1480 | 17300 | >90 | ~30 |

TABLE 6-continued

Estimated Occupancy of the Human σ1R and
D2R Receptors at Various Pridopidine Doses

| Species | Dose | Cmax (ng/ml) | AUC0-24 (h*ng/ml) | % σ1R occupancy | % D2R occupancy |
|---|---|---|---|---|---|
| | 150 mg BID[a] (300 mg/day, PO) | 2550 | 48400 | >90 | >40 |

Abbreviations: AUC, area under the curve; BID, twice daily; Cmax, observed maximum plasma or serum concentration after administration;; PET, positron-emission tomography; PO, per oral.
Human Cmax and AUC values for 45 and 90 mg BID are from Pride-HD (Study TV7820-CNS-20002) and simulated for 150 mg BID. Human σ1R and D$_2$R occupancy at 45 mg BID derived from human PET study TV7820-IMG-10082 and estimated for higher doses.
[a]Simulated data using the population pharmacokinetic modelling From Tables 2 and 6, it is clear that in the macaques, plasma exposures following the ineffective pridopidine dose (15 mg/kg) are associated with full $\sigma_1R$ (>85%) suggesting $\sigma_1R$ engagement alone is unlikely to account for the antidyskinetic benefits of pridopidine that were observed. Exposures following effective doses (20 to 30 mg/kg), while still providing full σ-1-occupancy, provide only modest D$_2$R-occupancy (25-40%). On the other hand, effective pridopidine doses clearly engage a range of receptors (including adrenergic-$\alpha_2$C, dopamine-D$_3$ and serotoninergic-5-HT$_{1A}$ sites) to a greater degree than D2 (Johnston et al 2018).

It is hypothesized that the ability of pridopidine to reduce PD-LID possibly involves a complex pharmacological profile, associated with high σ1R occupancy together with multiple non-sigma receptors, including adrenergic $\alpha_2$C, 5-HT$_{1A}$, and DA receptors.

Example 8: Treatment of Levodopa-Induced Dyskinesia (LID) in Patients with Parkinson's Disease (PD)

This is a 14-week, Phase 2B, multicenter, randomized, double-blind, placebo-controlled, three-arm, parallel-group study to evaluate the efficacy, safety, and PK of pridopidine 100 mg bid (oral capsule) and 150 mg bid (oral capsule) vs placebo for the treatment of PD-LID (Levodopa-Induced Dyskinesia in Patients with Parkinson's Disease),
Study Objectives
Primary Objective: To evaluate the efficacy of 2 dosages of pridopidine (100 mg twice daily bid and 150 mg bid) vs placebo for the treatment of PD-LID.
Inclusion Criteria
Patients may be included in the study only if they meet the following criteria:
  Has clinical diagnosis of Parkinson's Disease (PD).
  Has mild-to-moderate Levodopa-induced dyskinesia (LID).
Efficacy Endpoints
Primary endpoint will be assessed for both the 100 mg bid and the 150 mg bid pridopidine dosages vs placebo in a hierarchical manner.
Primary Endpoint/Outcome Measure:
The primary endpoint is the mean change from Baseline (Visit 2) to Visit 7/ET in the sum of Parts 1, 3, and 4 of the Unified Dyskinesia Rating Scale (UDysRS) dose dyskinesia.

REFERENCES

"Huntexil®" The NeurosSearch website, retrieved Sep. 24, 2012, http://neurosearch.com/Default.aspx?ID=8172.
Amantadine PDR 2017 Amantadine hydrochloride—Drug Summary, PDR (Prescribers' Digital Reference), http://www.pdr.net/drug-summary/Amantadine-Hydrochloride-Tablets-amantadine-hydrochloride-2441 and http://www.pdr.net/drug-summary/Amantadine-Hydrochloride-Capsules-amantadine-hydrochloride-1475 accessed Sep. 7, 2017
Bargiotas P. and Konitsiotis S. 2013. Levodopa-induced dyskinesias in Parkinson's disease: emerging treatments. Neuropsychiatric Disease and Treatment. 9:1605-1617
Brod et al. 2000 Combination therapy with glatiramer acetate (copolymer-1) and a type I interferon (IFN-α) does not improve experimental autoimmune encephalomyelitis. Annals of Neurology, 47:127-131.
Brust et al. 2014. Molecular Imaging of al Receptors In Vivo: Current Status and Perspectives. Curr. Med. Chem. 21, 35-69.
CSID:25948790, www.chemspider.com/Chemical-Structure.25948790.html (accessed 23:27, Jul. 15, 2016).
CSID:7971505, www.chemspider.com/Chemical-Structure.7971505.html (accessed 23:33, Jul. 15, 2016).
Cubo et al. 2001. Early morning off-medication dyskinesias, dystonia, and choreic subtypes. Arch. Neurol. 58(9):1379-1382.
Daneault, J-F. 2013. Drug-induced dyskinesia in Parkinson's disease. Should success in clinical management be a function of improvement of motor repertoire rather than amplitude of dyskinesia? BMC Medicine, 11:76.
Dizdar, N., et al., 1999. Human pharmacokinetics of L-3,4-dihydroxyphenylalanine studied with microdialysis. Clin Chem 45, 1813-1820.
Ecdeu, G W. 1976. Abnormal Involuntary Movement Scale (AIMS) Assessment Manual for Psychopharmacology: Revised (DHEW publication number ADM 76-338). Rockville, Md., US Department of Health, Education and Welfare, Public Health Service, Alcohol, Drug Abuse and Mental Health Administration, NIMH Psychopharmacology Research Branch, Division of Extramural Research Programs, 1976: 534-7
Gerber P E, Lynd L D. 1998. Selective serotonin-reuptake inhibitor-induced movement disorders. Ann Pharmacother 32: 692-698
Geva M, et al., 2016. Pridopidine activates neuroprotective pathways impaired in Huntington Disease. Hum Mol Genet. 25(18):3975-3987.
Goetz et al; 2007. Movement Disorder Society-sponsored revision of the Unified Parkinson's Disease Rating Scale (MDS-UPDRS): Process, format, and clinimetric testing plan. Movement Disorders 22(1):41-7.
Goetz et al; 2008a. Movement Disorder Society-sponsored revision of the Unified Parkinson's Disease Rating Scale (MDS-UPDRS): Scale Presentation and Clinimetric Testing Results. Movement Disorders 23(15):2129-2170.
Goetz, et al. 2008b. The Unified Dyskinesia Rating Scale: Presentation and Clinimetric Profile. Movement Disorders 23(16):2398-2403
Goetz, et al, 2013 Which Dyskinesia Scale Best Detects Treatment Response? Movement Disorders 28(3):341-346 Hauser, et al. 2004. Parkinson's disease home diary: Further validation and implications for clinical trials. Movement Dis. 19(12): 1409-1413.
Huot, P, et al, 2012. L-DOPA pharmacokinetics in the MPTP-lesioned macaque model of Parkinson's disease. Neuropharmacology 63, 829-836.
Huot P, et al. 2013 The pharmacology of L-DOPA-induced dyskinesia in Parkinson's disease. Pharmacol Rev 65: 171-222.
Jenner, P. 2008. Molecular mechanisms of L-DOPA-induced dyskinesia. Nature Reviews Neuroscience 9: 665-677.

Johnston, T H et al. and Lee, C S. 2001. "Levodopa-induced dyskinesia: Mechanisms and management" BCMJ 43(4), 206-9

Johnston, T H, et al, 2013. TC-8831, a nicotinic acetylcholine receptor agonist, reduces L-DOPA-induced dyskinesia in the MPTP macaque. Neuropharmacology 73, 337-347.

Kumar, N., et al., 2005 Levodopa-dyskinesia incidence by age of Parkinson's disease onset. Mov Disord. 20, 342-344.

Manson, A., et al., 2012 Levodopa-induced-dyskinesias clinical features, incidence, risk factors, management and impact on quality of life. J Parkinsons Dis 2, 189-198

Marder K, et al. 2000. Rate of functional decline in Huntington's disease. Neurology 54:452-458.

Movement Disorder Society Task Force on Rating Scales for Parkinson's Disease. 2003. Unified Parkinson's Disease Rating Scale (UPDRS): status and recommendations. Movement Disorders 18(7):738-50.

National Research Council Institute for Laboratory Animal, R., Guide for the Care and Use of Laboratory Animals. National Academies Press (US). Copyright 1996 by the National Academy of Sciences. All rights reserved, Washington (DC).

Poewe, W., Mahlknecht, P., 2009. The clinical progression of Parkinson's disease. Parkinsonism Relat Disord. 15 Suppl 4, S28-32.

Ponten H, et al. 2010. In vivo pharmacology of the dopaminergic stabilizer pridopidine. Eur J Pharmacol. 644(1-3):88-95.

Ponten H, et al. 2013. The dopaminergic stabilizer pridopidine decreases expression of L-DOPA-induced locomotor sensitisation in the rat unilateral 6-OHDA model. Eur J Pharmacol. 698(1-3):278-85.

Sahlholm K, et al. 2013. The dopamine stabilizers ACR16 and (−)-OSU6162 display nanomolar affinities at the σ-1 receptor. Mol Psychiatry. 18:12-14.

Sahlholm K, et al. 2015. Pridopidine selectively occupies sigma-1 rather than dopamine D2 receptors at behaviorally active doses. Psychopharmacol (Berl) 232(18):3443-3453.

Shoulson and Fahn. 1979. Huntington disease: clinical care and evaluation. Neurology 29:1-3.

Slifstein et al. 2010. Striatal and Extrastriatal Dopamine Release Measured With PET and [F-18] Fallypride. Synapse 64(5):350-62.

Tedroff, J, et al. 2004. A pilot study of the novel dopamine stabiliser ACR16 in advanced Parkinson's disease. Movement Disorders, Vol. 19, Suppl. 9, P565.

Thanvi, B. et al. 2007. Levodopa-induced dyskinesia in Parkinson's disease: clinical features, pathogenesis, prevention and treatment. Postgrad Med J; 83:384-388.

U.S. Pat. No. RE46117 (Sonesson, et al.)

U.S. Pat. No. 7,923,459, issued Apr. 12, 2011 (Gauthier, et al.)

PCT International Application Publication No. WO2014/205229

PCT International Application Publication No. WO 2017/015609

PCT International Application Publication No. WO2018/039477

Johnston T H, Geva M. Steiner L, Orbach A, Papapetropoulos S., Savola J M, et al. Pridopidine, a clinic-ready compound, reduced 3,4-dihydroxyphenylalanine-induced dyskinesia in parkinsonian macaques. Mov. Disord. Equb 2018 Dec. 21.

What is claimed is:

1. A method of treating levodopa-induced dyskinesia (LID) in a subject in need thereof, comprising administering to the subject an amount of pridopidine or pharmaceutically acceptable salt thereof, effective to treat the subject, wherein the amount of between 150-400 mg/day.

2. The method of claim 1, wherein the subject is afflicted with Parkinson's disease.

3. The method of claim 1, wherein the subject is afflicted with parkinsonism other than Parkinson's disease.

4. The method of claim 1, wherein the subject is concurrently being treated with levodopa.

5. The method of claim 4 wherein pridopidine and the levodopa are administered simultaneously.

6. The method of claim 5 wherein pridopidine and the levodopa are co-formulated.

7. The method of claim 4, wherein the pridopidine and the levodopa are administered sequentially and in separate pharmaceutical formulations.

8. The method of claim 1, wherein the amount of pridopidine is effective to alleviate or reduce a symptom associated with the levodopa treatment.

9. The method of claim 8, wherein the symptom is abnormal movements, myoclonic jerks, irregular movements of extremities, gait, facial grimacing, ataxia, inability to sustain motor act, hand movement or balance, choreiform peak dose dyskinesia, or dystonic peak dose dyskinesia.

10. The method of claim 8, wherein the symptom is bad quality on-time evoked by levodopa.

11. The method of claim 8, wherein the administration of pridopidine improves the symptom of the levodopa induced dyskinesia by at least 8%, by at least 20%, by at least 30% or by at least 50% as measured by MDS-UPDRS or UDysRS.

12. The method of claim 1, wherein the pridopidine is administered via oral administration.

13. The method of claim 1, wherein pridopidine is administered once or twice daily.

14. The method of claim 1, wherein the pridopidine is administered in the form of a pridopidine salt.

15. The method of claim 14, wherein the pridopidine salt is pridopidine hydrochloride.

16. The method of claim 1, wherein the pridopidine is administered at a daily dose of 200 mg given in the form of pridopidine HCl.

17. The method of claim 1, wherein the pridopidine is administered in equal doses, twice daily, thrice daily or four times daily.

18. The method of claim 1, wherein the $AUC_{0-24}$ achieved is about 25,000 h*ng/ml to about 60,000 h*ng/ml.

19. The method of claim 1, further delaying the onset of LID or reduce the risk of developing LID.

20. The method of claim 1, wherein the subject is receiving levodopa for treatment of Parkinson's disease.

* * * * *